(12) United States Patent
Vijayan et al.

(10) Patent No.: US 11,976,323 B2
(45) Date of Patent: May 7, 2024

(54) METHOD OF NUCLEIC ACID SEQUENCE DETERMINATION

(71) Applicant: Omniome, Inc., San Diego, CA (US)

(72) Inventors: Kandaswamy Vijayan, San Diego, CA (US); Pinar Iyidogan, San Diego, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 996 days.

(21) Appl. No.: 16/736,071

(22) Filed: Jan. 7, 2020

(65) Prior Publication Data

US 2020/0199668 A1      Jun. 25, 2020

Related U.S. Application Data

(63) Continuation of application No. 15/581,822, filed on Apr. 28, 2017, now Pat. No. 10,584,379.

(60) Provisional application No. 62/444,733, filed on Jan. 10, 2017, provisional application No. 62/329,489, filed on Apr. 29, 2016.

(51) Int. Cl.
| | | |
|---|---|---|
| C12Q 1/68 | (2018.01) | |
| C12N 9/12 | (2006.01) | |
| C12Q 1/6869 | (2018.01) | |
| C12Q 1/6874 | (2018.01) | |

(52) U.S. Cl.
CPC ......... *C12Q 1/6869* (2013.01); *C12N 9/1247* (2013.01); *C12Q 1/6874* (2013.01); *C12Y 207/07006* (2013.01)

(58) Field of Classification Search
CPC ............... C12Q 1/6869; C12N 9/1247; C12Y 207/07006
See application file for complete search history.

(56) References Cited

U.S. PATENT DOCUMENTS

| | | |
|---|---|---|
| 7,057,026 B2 | 6/2006 | Barnes et al. |
| 7,264,934 B2 | 9/2007 | Fuller |
| 7,414,116 B2 | 8/2008 | Milton et al. |
| 7,427,673 B2 | 9/2008 | Balasubramanian et al. |
| 7,476,503 B2 | 1/2009 | Turner et al. |
| 7,482,120 B2 | 1/2009 | Buzby |
| 7,544,794 B1 | 6/2009 | Benner |
| 8,071,755 B2 | 12/2011 | Efcavitch et al. |
| 8,133,672 B2 | 3/2012 | Bjornson et al. |
| 8,236,532 B2 | 8/2012 | Ronaghi et al. |
| 8,632,975 B2 | 1/2014 | Vander Horn et al. |
| 8,652,781 B2 | 2/2014 | Korlach et al. |
| 8,703,461 B2 | 4/2014 | Peris et al. |
| 9,279,155 B2 | 3/2016 | Bjornson et al. |
| 9,279,154 B2 | 6/2016 | Previte et al. |
| 9,556,480 B2 | 1/2017 | Turner et al. |
| 9,567,629 B2 | 2/2017 | Nikiforov |
| 10,240,134 B2 | 3/2019 | Vander Horn et al. |
| 2014/0186894 A1 | 7/2014 | Liu et al. |
| 2017/0022553 A1 | 1/2017 | Vijayan et al. |
| 2017/0314072 A1 | 11/2017 | Vijayan et al. |
| 2018/0155698 A1 | 6/2018 | Iyidogan et al. |

FOREIGN PATENT DOCUMENTS

| | | |
|---|---|---|
| JP | 2008502369 A | 1/2008 |
| WO | 9106678 | 5/1991 |
| WO | 2005019476 | 3/2005 |
| WO | 2007091077 | 8/2007 |
| WO | 2007123744 | 11/2007 |
| WO | 2008046612 | 4/2008 |
| WO | 2009010251 | 1/2009 |
| WO | 2009145820 | 12/2009 |
| WO | 2009145828 | 12/2009 |
| WO | 2010141390 | 12/2010 |
| WO | 2013023176 | 2/2013 |
| WO | 2014114665 | 7/2014 |
| WO | 2017190012 | 11/2017 |

OTHER PUBLICATIONS

KR2018-7034503, "Office Action", dated Jan. 17, 2020, 4 pages, with machine translation.
AU2018208462, "First Examination Report", dated Oct. 28, 2020, 4 pages.
Castro et al., "Nucleic Acid Polymerases Use a General Acid for Nucleotidyl Transfer", Nature Structural & Molecular Biology, vol. 16, Issue 2, Feb. 2009, pp. 212-218.
EP17722356.7, "Notice of Decision to Grant", dated Oct. 8, 2020, 2 pages.
JP2018-556287, "Office Action", dated Oct. 27, 2020, 6 pages.
Polesky et al., "Identification of Residues Critical for the Polymerase Activity of the Klenow Fragment of DNA Polymerase I from *Escherichia coli*", Journal of Biological Chemistry, vol. 265, Issue 24, Aug. 25, 1990, pp. 14579-14591.
KR2018-7034503, Office Action, dated Jul. 28, 2020, 5 pages.
CA3,049,722, Office Action, dated Jun. 23, 2020, 5 pages.
UniProt Accession No. D9N168_GEOSE, UniProtKB-UniRule, Oct. 5, 2010, 6 pages.
U.S. Appl. No. 15/581,822, "Non-Final Office Action", dated May 17, 2019, 13 pages.

(Continued)

*Primary Examiner* — Stephanie K Mummert
(74) *Attorney, Agent, or Firm* — Kilpatrick Townsend & Stockton LLP

(57) ABSTRACT

Provided are sequencing-by-binding methods of detecting cognate nucleotides using a crippled DNA polymerizing enzyme that possesses the ability to bind the next correct nucleotide downstream of a primer in a template-dependent fashion, but does not possess the activity needed to promote phosphodiester bond formation. Use of the crippled DNA polymerase permits interrogation of one nucleotide at a time, without incorporation of any nucleotide. Labeled nucleotides, such as fluorescently labeled nucleotides, can be used in conjunction with the crippled DNA polymerase to establish cognate nucleotide identity in a rapid manner.

9 Claims, 1 Drawing Sheet
Specification includes a Sequence Listing.

(56) References Cited

OTHER PUBLICATIONS

U.S. Appl. No. 15/581,822, "Notice of Allowance", dated Nov. 29, 2019, 9 pages.
U.S. Appl. No. 15/581,822, "Restriction Requirement", dated Jan. 30, 2019, 9 pages.
U.S. Appl. No. 15/866,353, "Non-Final Office Action", dated Oct. 21, 2019, 7 pages.
U.S. Appl. No. 15/866,353, "Notice of Allowance", dated Nov. 15, 2019, 8 pages.
Anker et al., "Biosensing with Plasmonic Nanosensors", Nature Materials, vol. 7, Issue No. 6, Jun. 2008, pp. 442-453.
Bibillo et al., "Functional Roles of Carboxylate Residues Comprising the DNA Polymerase Active Site Triad of Ty3 Reverse Transcriptase", Nucleic Acids Research, vol. 33, No. 1, 2005, pp. 171-181.
Brockman et al., "A Multistep Chemical Modification Procedure to Create DNA Arrays on Gold Surfaces for the Study of Protein—DNA Interactions with Surface Plasmon Resonance Imaging", Journal of the American Chemical Society, vol. 121, 1999, pp. 8044-8051.
Brown et al., "Pre-Steady-State Kinetic Analysis of Truncated and Full-Length *Saccharomyces cerevisiae* DNA Polymerase Eta", Journal of Nucleic Acids, vol. 2010, Article ID 871939, 2010, 11 pages.
CA3,022,431, "Office Action", dated Oct. 21, 2019, 4 pages.
Chen et al., "The history and advances of reversible terminators used in new generations of sequencing technology", Genomics, Proteomics & Bioinformatics 11(1), 2013, 34-40.
EP17722356.7, "Office Action", dated Dec. 16, 2019, 4 pages.
Escobedo et al., "Integrated Nanohole Array Surface Plasmon Resonance Sensing Device Using a Dual-Wavelength Source", Journal of Micromechanics and Microengineering, vol. 21, Issue No. 11, 2011, pp. 1-6.
Gangurde et al., "A Carboxylate Triad is Essential for the Polymerase Activity of *Escherichia coli* DNA Polymerase I (Klenow Fragment) Presence of two Functional Triads at the Catalytic Center", Journal of Biological Chemistry, vol. 275, No. 26, 2000, pp. 19685-19692.
Kaushik et al., "Biochemical Analysis of Catalytically Crucial Aspartate Mutants of Human Immunodeficiency Virus Type 1 Reverse Transcriptase", Biochemistry, vol. 35, 1996, pp. 11536-11546.
Kim, "An FET-type Charge Sensor for Highly Sensitive Detection of DNA Sequence", Biosensors and Bioelectronics, vol. 20, Issue No. 1, 2004, pp. 69-74.
Knapp et al., "Fluoride-Cleavable, Fluorescently Labelled Reversible Terminators: Synthesis and Use in Primer Extension", Chemistry—A European Journal, vol. 17, Issue 10, Mar. 2011, pp. 2903-2915.
Ma et al., "Enhancement of Polymerase Activity of the Large Fragment in DNA Polymerase I from Geobacillus stearothermophilus by Site-Directed Mutagenesis at the Active Site", Biomed Research International, Jan. 1, 2016, pp. 1-8.
Markiewicz et al., "Single-Molecule Microscopy Reveals New Insights into Nucleotide Selection by DNA Polymerase I", Nucleic Acids Research, vol. 40, Issue No. 16, Jun. 4, 2012, pp. 7975-7984.
Murphy et al., "A Triad Interaction in the Fingers Subdomain of DNA Polymerase Beta Controls Polymerase Activity", Journal of the American Chemical Society, vol. 133, No. 16, Apr. 27, 2011, 24 pages.
Nazirizadeh et al., "Low-Cost Label-Free Biosensors Using Photonic Crystals Embedded Between Crossed Polarizers", Optics Express, vol. 18, Issue No. 18, Aug. 30, 2010, pp. 19120-19128.
Patel, "Insights into DNA Polymerization Mechanisms from Structure and Function Analysis of HIV-1 Reverse Transcriptase.", Biochemistry, vol. 34, 1995, pp. 5351-5363.
PCT/US2017/030135, "International Preliminary Report on Patentability", dated Nov. 8, 2018, 8 pages.
PCT/US2017/030135, "International Search Report and Written Opinion", dated Jul. 21, 2017, 12 pages.
PCT/US2018/013007, "International Preliminary Report on Patentability", dated Jul. 25, 2019, 11 pages.
PCT/US2018/013007, "International Search Report and Written Opinion", dated Jun. 20, 2018, 18 pages.
PCT/US2018/013007, "International Search Report and Written Opinion", dated May 14, 2018, 18 pages.
PCT/US2018/013007, "Invitation to Pay Add'l Fees and Partial Search Report", dated Mar. 19, 2018, 6 pages.
Roettger et al., "Mismatched and Matched dNTP Incorporation by DNA Polymerase β Proceed via Analogues Kinetic Pathways", Biochemistry, vol. 47, Issue No. 37, 2008, pp. 9718-9727.
Sandalli et al., "Characterization of Catalytic Carboxylate Triad in Non-Replicative DNA Polymerase III (Pol E) Of Geobacillus Kaustophilus HTA", Cellular and Molecular Biology, vol. 58, No. 1, Dec. 22, 2012, pp. 44-49.
Schultz et al., "Single-Target Molecule Detection With Nonbleaching Multicolor Optical Immunolabels", PNAS, vol. 96, Issue No. 3, Feb. 1, 2000, pp. 996-1001.
SG11201809522w, "Written Opinion", dated Sep. 9, 2019, 10 pages.
Star et al., "Electronic Detection of Specific Protein Binding Using Nanotube FET Devices", Nano Letters, vol. 3, Issue No. 4, Apr. 1, 2003, pp. 459-463.
Tsai et al., "Site-Specific Labeling of T7 DNA Polymerase with a Conformationally Sensitive Flurophore and its Use in Detecting Single-Nucleotide Polymorphisms", Analytical Biochemistry, vol. 384, No. 1, Jan. 1, 2009, pp. 136-144.
Vaidyanathan et al., "Binding Kinetics of DNA-Protein Interaction Using Surface Plasmon Resonance", Protocol Exchange, May 22, 2013, 11 pages.
Walsh et al., "Synthetic Nucleotides as Probes of DNA Polymerase Specificity", Journal of Nucleic Acids, vol. 2012, Article ID 530963, Jun. 2012, 17 pages.
Washington et al., "Human DNA Polymerase Utilizes Different Nucleotide Incorporation Mechanisms Dependent upon the Template Base", Molecular and Cellular Biology, vol. 24, Issue No. 2, Jan. 2004, pp. 936-943.
Xia et al., "DNA Mismatch Synthesis Complexes Provide Insights into Base Selectivity of a B family DNA Polymerase", J Am Chem Soc. vol. 135, Issue 1, Jan. 9, 2013, pp. 193-202.
CA3,049,722, "Office Action", dated May 27, 2021, 2 pages.
CN201780026228.X, "Office Action", dated Apr. 28, 2021, 11 pages.
CA3,022,431, "Office Action", dated Dec. 3, 2020, 6 pages.
KR2018-7034503, "Notice of Decision to Grant", dated Feb. 9, 2021, 3 pages.
Nakamura et al., "Watching DNA Polymerase κ make a Phosphodiester Bond", Nature, vol. 487, No. 7406, Jul. 12, 2012, pp. 196-201.
Yang et al., "Making and Breaking Nucleic Acids: Two-Mg2+-ion Catalysis and Substrate Specificity", Molecular Cell, vol. 22, No. 1, Apr. 7, 2006, pp. 5-13.
AU2017258523, "First Examination Report", dated Jun. 18, 2020, 4 pages.
EP18701394.1, "Office Action", dated May 28, 2020, 4 pages.
CA3,022,431, "Office Action", dated Oct. 26, 2021, 2 pages.
U.S. Appl. No. 16/738,577, "Non-Final Office Action", dated Apr. 27, 2023, 11 pages.
U.S. Appl. No. 16/738,577, "Ex-Parte Quayle Action", Jan. 5, 2024, 7 pages.

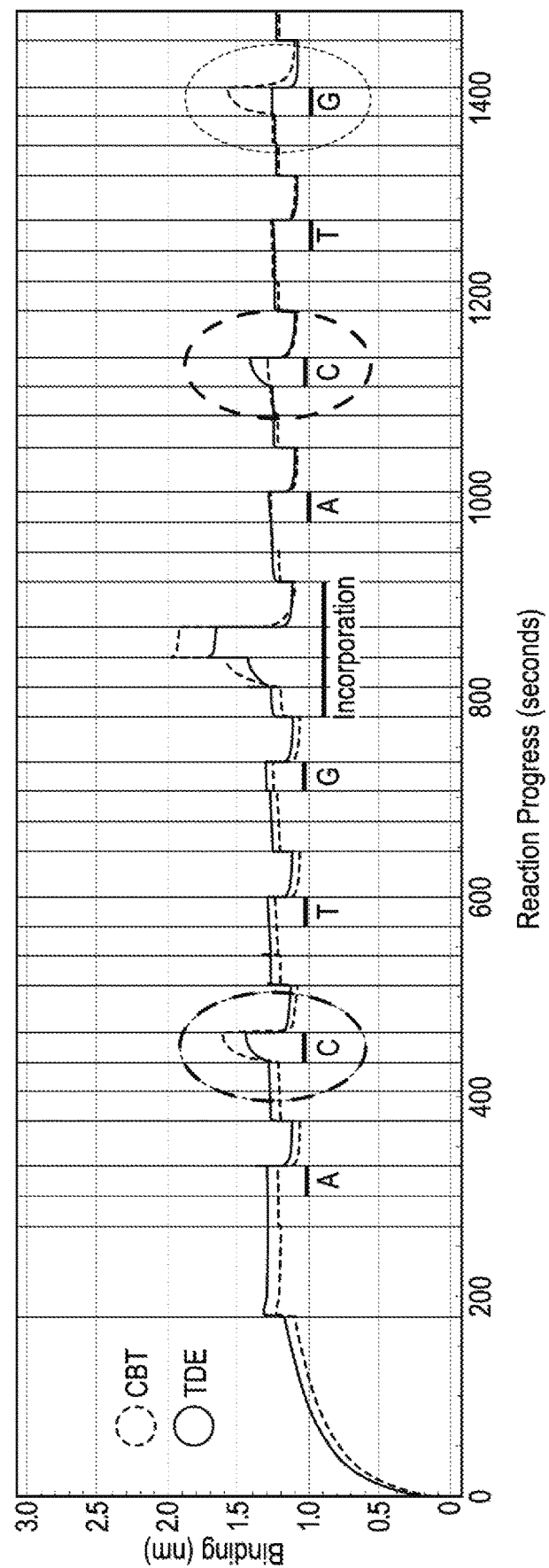

SEQUENCE LISTING

```
<160> NUMBER OF SEQ ID NOS: 15

<210> SEQ ID NO 1
<211> LENGTH: 604
<212> TYPE: PRT
<213> ORGANISM: Artificial Sequence
<220> FEATURE:
<223> OTHER INFORMATION: Engineered DNA polymerase

<400> SEQUENCE: 1

Met Gly Ser Ser His His His His His His Ser Ser Gly Leu Val Pro
1               5                   10                  15

Arg Gly Ser His Met Ser Cys Gly Ala Ala Met Ala Phe Thr Leu Ala
            20                  25                  30

Asp Arg Val Thr Glu Glu Met Leu Ala Asp Lys Ala Ala Leu Val Val
        35                  40                  45

Glu Val Val Glu Glu Asn Tyr His Asp Ala Pro Ile Val Gly Ile Ala
    50                  55                  60

Val Val Asn Glu His Gly Arg Phe Phe Leu Arg Pro Glu Thr Ala Leu
65                  70                  75                  80

Ala Asp Pro Gln Phe Val Ala Trp Leu Gly Asp Glu Thr Lys Lys Lys
                85                  90                  95

Ser Met Phe Asp Ser Lys Arg Ala Ala Val Ala Leu Lys Trp Lys Gly
            100                 105                 110
```

```
Ile Glu Leu Ala Gly Val Ser Phe Asp Leu Leu Ala Ala Tyr Leu
        115                 120                 125

Leu Asp Pro Ala Gln Gly Val Asp Val Ala Ala Ala Lys Met
130                 135                 140

Lys Gln Tyr Glu Ala Val Arg Pro Asp Glu Ala Val Tyr Gly Lys Gly
145                 150                 155                 160

Ala Lys Arg Ala Val Pro Asp Glu Pro Val Leu Ala Glu His Leu Val
                165                 170                 175

Arg Lys Ala Ala Ala Ile Trp Glu Leu Glu Arg Pro Phe Leu Asp Glu
                180                 185                 190

Leu Arg Arg Asn Glu Gln Asp Arg Leu Leu Val Glu Leu Glu Gln Pro
        195                 200                 205

Leu Ser Ser Ile Leu Ala Glu Met Glu Phe Ala Gly Val Lys Val Asp
        210                 215                 220

Thr Lys Arg Leu Glu Gln Met Gly Lys Glu Leu Ala Glu Gln Leu Gly
225                 230                 235                 240

Thr Val Glu Gln Arg Ile Tyr Glu Leu Ala Gly Gln Glu Phe Asn Ile
                245                 250                 255

Asn Ser Pro Lys Gln Leu Gly Val Ile Leu Phe Glu Lys Leu Gln Leu
                260                 265                 270

Pro Val Leu Lys Lys Thr Lys Thr Gly Tyr Ser Thr Ser Ala Asp Val
        275                 280                 285

Leu Glu Lys Leu Ala Pro Tyr His Glu Ile Val Glu Asn Ile Leu His
        290                 295                 300

Tyr Arg Gln Leu Gly Lys Leu Gln Ser Thr Tyr Ile Glu Gly Leu Leu
305                 310                 315                 320

Lys Val Val Arg Pro Ala Thr Lys Lys Val His Thr Ile Phe Asn Gln
                325                 330                 335

Ala Leu Thr Gln Thr Gly Arg Leu Ser Ser Thr Glu Pro Asn Leu Gln
                340                 345                 350

Asn Ile Pro Ile Arg Leu Glu Glu Gly Arg Lys Ile Arg Gln Ala Phe
        355                 360                 365

Val Pro Ser Glu Ser Asp Trp Leu Ile Phe Ala Ala Asp Tyr Ser Gln
        370                 375                 380

Ile Glu Leu Arg Val Leu Ala His Ile Ala Glu Asp Asp Asn Leu Met
385                 390                 395                 400

Glu Ala Phe Arg Arg Asp Leu Asp Ile His Thr Lys Thr Ala Met Asp
                405                 410                 415

Ile Phe Gln Val Ser Glu Asp Glu Val Thr Pro Asn Met Arg Arg Gln
                420                 425                 430

Ala Lys Ala Val Asn Tyr Gly Ile Val Tyr Gly Ile Ser Asp Tyr Gly
        435                 440                 445

Leu Ala Gln Asn Leu Asn Ile Ser Arg Lys Glu Ala Ala Glu Phe Ile
        450                 455                 460

Glu Arg Tyr Phe Glu Ser Phe Pro Gly Val Lys Arg Tyr Met Glu Asn
465                 470                 475                 480

Ile Val Gln Glu Ala Lys Gln Lys Gly Tyr Val Thr Thr Leu Leu His
                485                 490                 495

Arg Arg Arg Tyr Leu Pro Asp Ile Thr Ser Arg Asn Phe Asn Val Arg
                500                 505                 510

Ser Phe Ala Glu Arg Met Ala Met Asn Thr Pro Ile Gln Gly Ser Ala
        515                 520                 525
```

```
Ala Asp Ile Ile Lys Lys Ala Met Ile Asp Leu Asn Ala Arg Leu Lys
    530                 535                 540

Glu Glu Arg Leu Gln Ala His Leu Leu Leu Gln Val His Asp Glu Leu
545                 550                 555                 560

Ile Leu Glu Ala Pro Lys Glu Glu Met Glu Arg Leu Ala Arg Leu Val
                565                 570                 575

Pro Glu Val Met Glu Gln Ala Val Thr Leu Arg Val Pro Leu Lys Val
            580                 585                 590

Asp Tyr His Tyr Gly Ser Thr Trp Tyr Asp Ala Lys
        595                 600

<210> SEQ ID NO 2
<211> LENGTH: 587
<212> TYPE: PRT
<213> ORGANISM: Artificial Sequence
<220> FEATURE:
<223> OTHER INFORMATION: Engineered DNA polymerase
<220> FEATURE:
<221> NAME/KEY: MISC_FEATURE
<223> OTHER INFORMATION: Engineered DNA polymerase

<400> SEQUENCE: 2

Gly Ser His Met Ser Cys Gly Ala Ala Met Ala Phe Thr Leu Ala Asp
1               5                   10                  15

Arg Val Thr Glu Glu Met Leu Ala Asp Lys Ala Ala Leu Val Val Glu
            20                  25                  30

Val Val Glu Glu Asn Tyr His Asp Ala Pro Ile Val Gly Ile Ala Val
        35                  40                  45

Val Asn Glu His Gly Arg Phe Phe Leu Arg Pro Glu Thr Ala Leu Ala
50                  55                  60

Asp Pro Gln Phe Val Ala Trp Leu Gly Asp Glu Thr Lys Lys Lys Ser
65                  70                  75                  80

Met Phe Asp Ser Lys Arg Ala Ala Val Ala Leu Lys Trp Lys Gly Ile
                85                  90                  95

Glu Leu Ala Gly Val Ser Phe Asp Leu Leu Leu Ala Ala Tyr Leu Leu
            100                 105                 110

Asp Pro Ala Gln Gly Val Asp Asp Val Ala Ala Ala Lys Met Lys
        115                 120                 125

Gln Tyr Glu Ala Val Arg Pro Asp Glu Ala Val Tyr Gly Lys Gly Ala
130                 135                 140

Lys Arg Ala Val Pro Asp Glu Pro Val Leu Ala Glu His Leu Val Arg
145                 150                 155                 160

Lys Ala Ala Ala Ile Trp Glu Leu Glu Arg Pro Phe Leu Asp Glu Leu
                165                 170                 175

Arg Arg Asn Glu Gln Asp Arg Leu Leu Val Glu Leu Glu Gln Pro Leu
            180                 185                 190

Ser Ser Ile Leu Ala Glu Met Glu Phe Ala Gly Val Lys Val Asp Thr
        195                 200                 205

Lys Arg Leu Glu Gln Met Gly Lys Glu Leu Ala Glu Gln Leu Gly Thr
210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270
```

Glu Lys Leu Ala Pro Tyr His Glu Ile Val Glu Asn Ile Leu His Tyr
            275                 280                 285

Arg Gln Leu Gly Lys Leu Gln Ser Thr Tyr Ile Glu Gly Leu Leu Lys
        290                 295                 300

Val Val Arg Pro Ala Thr Lys Lys Val His Thr Ile Phe Asn Gln Ala
305                 310                 315                 320

Leu Thr Gln Thr Gly Arg Leu Ser Ser Thr Glu Pro Asn Leu Gln Asn
                325                 330                 335

Ile Pro Ile Arg Leu Glu Glu Gly Arg Lys Ile Arg Gln Ala Phe Val
            340                 345                 350

Pro Ser Glu Ser Asp Trp Leu Ile Phe Ala Ala Asp Tyr Ser Gln Ile
        355                 360                 365

Glu Leu Arg Val Leu Ala His Ile Ala Glu Asp Asp Asn Leu Met Glu
    370                 375                 380

Ala Phe Arg Arg Asp Leu Asp Ile His Thr Lys Thr Ala Met Asp Ile
385                 390                 395                 400

Phe Gln Val Ser Glu Asp Glu Val Thr Pro Asn Met Arg Arg Gln Ala
                405                 410                 415

Lys Ala Val Asn Tyr Gly Ile Val Tyr Gly Ile Ser Asp Tyr Gly Leu
            420                 425                 430

Ala Gln Asn Leu Asn Ile Ser Arg Lys Glu Ala Ala Glu Phe Ile Glu
        435                 440                 445

Arg Tyr Phe Glu Ser Phe Pro Gly Val Lys Arg Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Asn Ala Arg Leu Lys Glu
        515                 520                 525

Glu Arg Leu Gln Ala His Leu Leu Leu Gln Val His Asp Glu Leu Ile
    530                 535                 540

Leu Glu Ala Pro Lys Glu Glu Met Glu Arg Leu Ala Arg Leu Val Pro
545                 550                 555                 560

Glu Val Met Glu Gln Ala Val Thr Leu Arg Val Pro Leu Lys Val Asp
                565                 570                 575

Tyr His Tyr Gly Ser Thr Trp Tyr Asp Ala Lys
            580                 585

<210> SEQ ID NO 3
<211> LENGTH: 578
<212> TYPE: PRT
<213> ORGANISM: Artificial Sequence
<220> FEATURE:
<223> OTHER INFORMATION: Engineered DNA polymerase

<400> SEQUENCE: 3

Met Ala Phe Thr Leu Ala Asp Arg Val Thr Glu Glu Met Leu Ala Asp
1               5                   10                  15

Lys Ala Ala Leu Val Val Glu Val Val Glu Glu Asn Tyr His Asp Ala
                20                  25                  30

Pro Ile Val Gly Ile Ala Val Val Asn Glu His Gly Arg Phe Phe Leu
            35                  40                  45

```
Arg Pro Glu Thr Ala Leu Ala Asp Pro Gln Phe Val Ala Trp Leu Gly
    50                  55                  60

Asp Glu Thr Lys Lys Lys Ser Met Phe Asp Ser Lys Arg Ala Ala Val
65                  70                  75                  80

Ala Leu Lys Trp Lys Gly Ile Glu Leu Ala Gly Val Ser Phe Asp Leu
                    85                  90                  95

Leu Leu Ala Ala Tyr Leu Leu Asp Pro Ala Gln Gly Val Asp Asp Val
            100                 105                 110

Ala Ala Ala Lys Met Lys Gln Tyr Glu Ala Val Arg Pro Asp Glu
            115                 120                 125

Ala Val Tyr Gly Lys Gly Ala Lys Arg Ala Val Pro Asp Glu Pro Val
    130                 135                 140

Leu Ala Glu His Leu Val Arg Lys Ala Ala Ile Trp Glu Leu Glu
145                 150                 155                 160

Arg Pro Phe Leu Asp Glu Leu Arg Arg Asn Glu Gln Asp Arg Leu Leu
                    165                 170                 175

Val Glu Leu Glu Gln Pro Leu Ser Ser Ile Leu Ala Glu Met Glu Phe
            180                 185                 190

Ala Gly Val Lys Val Asp Thr Lys Arg Leu Glu Gln Met Gly Lys Glu
            195                 200                 205

Leu Ala Glu Gln Leu Gly Thr Val Glu Gln Arg Ile Tyr Glu Leu Ala
    210                 215                 220

Gly Gln Glu Phe Asn Ile Asn Ser Pro Lys Gln Leu Gly Val Ile Leu
225                 230                 235                 240

Phe Glu Lys Leu Gln Leu Pro Val Leu Lys Lys Thr Lys Thr Gly Tyr
                    245                 250                 255

Ser Thr Ser Ala Asp Val Leu Glu Lys Leu Ala Pro Tyr His Glu Ile
            260                 265                 270

Val Glu Asn Ile Leu His Tyr Arg Gln Leu Gly Lys Leu Gln Ser Thr
            275                 280                 285

Tyr Ile Glu Gly Leu Leu Lys Val Val Arg Pro Ala Thr Lys Lys Val
    290                 295                 300

His Thr Ile Phe Asn Gln Ala Leu Thr Gln Thr Gly Arg Leu Ser Ser
305                 310                 315                 320

Thr Glu Pro Asn Leu Gln Asn Ile Pro Ile Arg Leu Glu Glu Gly Arg
                    325                 330                 335

Lys Ile Arg Gln Ala Phe Val Pro Ser Glu Ser Asp Trp Leu Ile Phe
            340                 345                 350

Ala Ala Asp Tyr Ser Gln Ile Glu Leu Arg Val Leu Ala His Ile Ala
            355                 360                 365

Glu Asp Asp Asn Leu Met Glu Ala Phe Arg Arg Asp Leu Asp Ile His
    370                 375                 380

Thr Lys Thr Ala Met Asp Ile Phe Gln Val Ser Glu Asp Glu Val Thr
385                 390                 395                 400

Pro Asn Met Arg Arg Gln Ala Lys Ala Val Asn Tyr Gly Ile Val Tyr
                    405                 410                 415

Gly Ile Ser Asp Tyr Gly Leu Ala Gln Asn Leu Asn Ile Ser Arg Lys
            420                 425                 430

Glu Ala Ala Glu Phe Ile Glu Arg Tyr Phe Glu Ser Phe Pro Gly Val
            435                 440                 445

Lys Arg Tyr Met Glu Asn Ile Val Gln Glu Ala Lys Gln Lys Gly Tyr
    450                 455                 460

Val Thr Thr Leu Leu His Arg Arg Arg Tyr Leu Pro Asp Ile Thr Ser
```

```
             465                 470                 475                 480
Arg Asn Phe Asn Val Arg Ser Phe Ala Glu Arg Met Ala Met Asn Thr
                485                 490                 495

Pro Ile Gln Gly Ser Ala Ala Asp Ile Ile Lys Lys Ala Met Ile Asp
                500                 505                 510

Leu Asn Ala Arg Leu Lys Glu Glu Arg Leu Gln Ala His Leu Leu Leu
                515                 520                 525

Gln Val His Asp Glu Leu Ile Leu Glu Ala Pro Lys Glu Glu Met Glu
                530                 535                 540

Arg Leu Ala Arg Leu Val Pro Glu Val Met Glu Gln Ala Val Thr Leu
545                 550                 555                 560

Arg Val Pro Leu Lys Val Asp Tyr His Tyr Gly Ser Thr Trp Tyr Asp
                565                 570                 575

Ala Lys

<210> SEQ ID NO 4
<211> LENGTH: 26
<212> TYPE: PRT
<213> ORGANISM: Escherichia coli

<400> SEQUENCE: 4

Asp Tyr Val Ile Val Ser Ala Asp Tyr Ser Gln Ile Glu Leu Arg Ile
1               5                   10                  15

Met Ala His Leu Ser Arg Asp Lys Gly Leu
            20                  25

<210> SEQ ID NO 5
<211> LENGTH: 26
<212> TYPE: PRT
<213> ORGANISM: Thermus aquaticus

<400> SEQUENCE: 5

Gly Trp Leu Leu Val Ala Leu Asp Tyr Ser Gln Ile Glu Leu Arg Val
1               5                   10                  15

Leu Ala His Leu Ser Gly Asp Glu Asn Leu
            20                  25

<210> SEQ ID NO 6
<211> LENGTH: 26
<212> TYPE: PRT
<213> ORGANISM: Bacillus stearothermophilus

<400> SEQUENCE: 6

Asp Trp Leu Ile Phe Ala Ala Asp Tyr Ser Gln Ile Glu Leu Arg Val
1               5                   10                  15

Leu Ala His Ile Ala Glu Asp Asp Asn Leu
            20                  25

<210> SEQ ID NO 7
<211> LENGTH: 26
<212> TYPE: PRT
<213> ORGANISM: Bacillus subtilis

<400> SEQUENCE: 7

Asp Trp Leu Ile Phe Ala Ala Asp Tyr Ser Gln Ile Glu Leu Arg Val
1               5                   10                  15

Leu Ala His Ile Ser Lys Asp Glu Asn Leu
            20                  25
```

```
<210> SEQ ID NO 8
<211> LENGTH: 19
<212> TYPE: PRT
<213> ORGANISM: Escherichia coli

<400> SEQUENCE: 8

Met Ile Met Gln Val His Asp Glu Leu Val Phe Glu Val His Lys Asp
1               5                   10                  15

Asp Val Asp

<210> SEQ ID NO 9
<211> LENGTH: 19
<212> TYPE: PRT
<213> ORGANISM: Thermus aquaticus

<400> SEQUENCE: 9

Met Leu Leu Gln Val His Asp Glu Leu Val Leu Glu Ala Pro Lys Glu
1               5                   10                  15

Arg Ala Glu

<210> SEQ ID NO 10
<211> LENGTH: 19
<212> TYPE: PRT
<213> ORGANISM: Bacillus stearothermophilus

<400> SEQUENCE: 10

Leu Leu Leu Gln Val His Asp Glu Leu Ile Leu Glu Ala Pro Lys Glu
1               5                   10                  15

Glu Ile Glu

<210> SEQ ID NO 11
<211> LENGTH: 19
<212> TYPE: PRT
<213> ORGANISM: Bacillus subtilis

<400> SEQUENCE: 11

Leu Leu Leu Gln Val His Asp Glu Leu Ile Phe Glu Ala Pro Lys Glu
1               5                   10                  15

Glu Ile Glu

<210> SEQ ID NO 12
<211> LENGTH: 8
<212> TYPE: PRT
<213> ORGANISM: Artificial Sequence
<220> FEATURE:
<223> OTHER INFORMATION: mutant of DNA polymerase motif A

<400> SEQUENCE: 12

Glu Tyr Ser Gln Ile Glu Leu Arg
1               5

<210> SEQ ID NO 13
<211> LENGTH: 8
<212> TYPE: PRT
<213> ORGANISM: Bacillus stearothermophilus

<400> SEQUENCE: 13

Asp Tyr Ser Gln Ile Glu Leu Arg
1               5

<210> SEQ ID NO 14
<211> LENGTH: 6
<212> TYPE: PRT
```

```
<213> ORGANISM: Artificial Sequence
<220> FEATURE:
<223> OTHER INFORMATION: Mutant of DNA polymerase motif C

<400> SEQUENCE: 14

Gln Val His Glu Glu Leu
1               5

<210> SEQ ID NO 15
<211> LENGTH: 6
<212> TYPE: PRT
<213> ORGANISM: Bacillus stearothermophilus

<400> SEQUENCE: 15

Gln Val His Asp Glu Leu
1               5
```

METHOD OF NUCLEIC ACID SEQUENCE DETERMINATION

RELATED APPLICATIONS

This application is a continuation of U.S. application Ser. No. 15/581,822, filed Apr. 28, 2017; which claims the benefit of U.S. Provisional Application No. 62/444,733, filed Jan. 10, 2017; and U.S. Provisional Application No. 62/329,489, filed Apr. 29, 2016. The disclosures of these earlier applications are hereby incorporated by reference in their entireties.

REFERENCE TO A "SEQUENCE LISTING" SUBMITTED AS ASCII TEXT FILE VIA EFS-WEB

The instant application contains a Sequence Listing which has been filed electronically in ASCII format and is hereby incorporated by reference in its entirety. Said ASCII copy, created on Mar. 6, 2020, is named OMN-013US2_Sequence_Listing_097128-1170322 and is 18,699 bytes in size.

TECHNICAL FIELD

The present invention relates generally to the field of biotechnology. More specifically, the invention concerns nucleic acid sequencing technology.

BACKGROUND

Accurate polynucleotide sequence determination is critically important in many applications. For example, comprehensive definition of an individual's genetic profile requires that long stretches of chromosomal DNA are determined and compared against databases of known sequences. The results can establish profiles of predispositions or susceptibilities to provide medical insights. Likewise, tumor profiling also can require accurate sequence determination to establish the efficacy of a drug treatment regimen before treatment has begun. As well, identifying bacterial, viral, or other pathogens from nucleic acid databases also can depend on accurate sequencing results.

Stretches of more than one of the same base along a strand of nucleic acid are among the factors confounding accurate sequence determination. These "homopolymer" stretches can be overlooked by some sequencing approaches, such that a single base will be detected when multiples actually are present. Some sequencing methods further can experience "phasing" issues that can be exacerbated by the homopolymer stretches. As a consequence of phasing, sequence determination downstream of a homopolymer stretch can be rendered ambiguous.

Different approaches have been developed to address and resolve homopolymer sequencing issues. Reversible terminator nucleotides have been employed to ensure that only a single nucleotide is enzymatically incorporated into a growing primer. While effective, follow-on steps can be required to remove the chemical terminator moiety from the primer before the next round of template-dependent incorporation can occur. Other approaches have involved measuring the amplitude of incorporation signals using only one species of nucleotide at a time. Unfortunately, this approach imposes limits on the length of sequence that can be determined. Thus, there remains a need for new approaches that can be used for sequencing nucleic acids, including accurate sequencing through homopolymer stretches within a nucleic acid strand.

BRIEF DESCRIPTION OF THE DRAWINGS

FIG. 1 is an interferometry trace showing the intensity of binding signal (vertical axis) as a function of time or reaction progress (horizontal axis). Traces are presented for a control polymerase ("CBT") and for an engineered polymerase ("TDE"). The CBT polymerase can form ternary complexes and incorporate cognate nucleotides. The engineered TDE polymerase retains the ability to form ternary complexes in the presence of cognate nucleotide, but cannot incorporate any nucleotide in the presence of the catalytic $Mg^{2+}$ metal ion. Identities of nucleotides tested in the binding reactions are indicated below the traces (A=dATP; C=dCTP; T=dTTP; G=dGTP). The trace showing the higher binding signal for dCTP, and the lower binding signal for dGTP following the incorporation step corresponds to the modified TDE polymerase.

SUMMARY OF THE DISCLOSURE

In a first aspect, the disclosure relates to a method of determining whether a test nucleotide is the next correct nucleotide having a base complementary to the next base in a template strand immediately downstream of a primer in a primed template nucleic acid. The method includes the step of (a) contacting the primed template nucleic acid with a first reaction mixture that includes a crippled DNA polymerase and the test nucleotide. As a result of the contact, if the test nucleotide is the next correct nucleotide, there is formed a complex that includes the primed template nucleic acid, the crippled DNA polymerase and the test nucleotide. The crippled DNA polymerase used in the method is substantially unable to catalyze formation of phosphodiester bonds in the presence of magnesium ions. There also is the step of (b) measuring binding of the primed template nucleic acid to the crippled DNA polymerase in the presence of the test nucleotide, without chemical incorporation of the test nucleotide into the primer of the primed template nucleic acid. Next, there is the step of (c) determining from the results of step (b) whether the test nucleotide is the next correct nucleotide. In one embodiment, the first reaction mixture includes a catalytic divalent metal ion. For example, the catalytic divalent metal ion can be $Mg^{2+}$ ion or $Mn^{2+}$ ion. In each case, the test nucleotide can include an exogenous label. Preferably, the exogenous label of the test nucleotide has a fluorescent moiety, and step (b) involves measuring a fluorescent signal produced by the fluorescent moiety of the test nucleotide. More preferably, the crippled DNA polymerase has an exogenous label, and step (b) involves detecting the exogenous label of the crippled DNA polymerase. When this is the case, the exogenous label of the crippled DNA polymerase can include a fluorescent moiety, and step (b) can involve measuring a fluorescent signal produced by the fluorescent moiety of the crippled DNA polymerase. Generally speaking, and with reference to any of the preceding embodiments, the primer can include a free 3' hydroxyl group. Still more generally, and with reference to any of the preceding embodiments, after step (b), there can be the additional step of replacing the first reaction mixture with a second reaction mixture that includes a second polymerase and a second type of nucleotide, and then incorporating the second type of nucleotide into the primer of the primed template nucleic acid. For example, the second type of nucleotide can be a reversible terminator nucleotide. Yet more generally, and with reference to any of the preceding embodiments, the first reaction mixture can include $Mg^{2+}$ ions, and the primer can include a 3' hydroxyl moiety. Indeed, the primer of the disclosed method can a 3' hydroxyl moiety.

In another aspect, the disclosure relates to an isolated mutant DNA polymerase that has the amino acid sequence of SEQ ID NO:12 in place of SEQ ID NO:13. The mutant DNA polymerase forms ternary complexes with primed template nucleic acid molecules and cognate nucleotides, and does not catalyze phosphodiester bond formation in the presence of $Mg^{2+}$ ion. Preferably, the isolated mutant DNA polymerase includes a reporter moiety attached thereto.

In another aspect, the disclosure relates to an isolated mutant DNA polymerase having the amino acid sequence of SEQ ID NO:14 in place of SEQ ID NO:15. The mutant DNA polymerase forms ternary complexes with primed template nucleic acid molecules and cognate nucleotides, and does not catalyze phosphodiester bond formation in the presence of $Mg^{2+}$ ion. Preferably, the isolated mutant DNA polymerase further includes a reporter moiety attached thereto.

In another aspect, the disclosure relates to an isolated mutant DNA polymerase having the amino acid sequence of SEQ ID NO:3, except for replacement of aspartate by glutamate at position 355. The mutant DNA polymerase forms ternary complexes with primed template nucleic acid molecules and cognate nucleotides, and does not catalyze phosphodiester bond formation in the presence of $Mg^{2+}$ ion. Preferably, the isolated mutant DNA polymerase further includes an N-terminal sequence of amino acids having a cysteine residue. More preferably, the cysteine residue is chemically linked to a detectable label.

In another aspect, the disclosure relates to an isolated mutant DNA polymerase having the amino acid sequence of SEQ ID NO:3, except for replacement of an aspartate residue by a glutamate residue at position 532. The mutant DNA polymerase forms ternary complexes with primed template nucleic acid molecules and cognate nucleotides, and does not catalyze phosphodiester bond formation in the presence of $Mg^{2+}$ ion. Preferably, isolated mutant DNA polymerase further includes an N-terminal sequence of amino acids having a cysteine residue. More preferably, the cysteine residue is chemically linked to a detectable label.

Further Aspects

Further aspects of the present disclosure are described in the following numbered paragraphs.

1. A method of determining whether a test nucleotide is the next correct nucleotide comprising a base complementary to the next base in a template strand immediately downstream of a primer in a primed template nucleic acid, comprising the steps of:
   (a) contacting the primed template nucleic acid with a first reaction mixture that comprises a crippled DNA polymerase and the test nucleotide,
   whereby, if the test nucleotide is the next correct nucleotide, there is formed a complex comprising the primed template nucleic acid, the crippled DNA polymerase and the test nucleotide, and
   wherein the crippled DNA polymerase is substantially incapable of magnesium-catalyzed phosphodiester bond formation;
   (b) measuring binding of the primed template nucleic acid to the crippled DNA polymerase in the presence of the test nucleotide, without chemical incorporation of the test nucleotide into the primer of the primed template nucleic acid; and
   (c) determining from the results of step (b) whether the test nucleotide is the next correct nucleotide.
2. The method of paragraph 1, wherein the crippled DNA polymerase comprises either a polypeptide sequence comprising SEQ ID NO:12, or a polypeptide sequence comprising SEQ ID NO:14.
3. The method of paragraph 1, wherein the crippled DNA polymerase catalyzes formation of phosphodiester bonds in the presence of divalent manganese ions, and wherein the first reaction mixture does not contain a concentration of divalent manganese ions that promotes formation of phosphodiester bonds.
4. The method of any one of paragraphs 1-3, wherein the test nucleotide comprises an exogenous label.
5. The method of paragraph 3, wherein the exogenous label of the test nucleotide comprises a fluorescent moiety, and wherein step (b) comprises measuring a fluorescent signal produced by the fluorescent moiety of the test nucleotide.
6. The method of any one of paragraphs 1-5, wherein the crippled DNA polymerase comprises an exogenous label, and wherein step (b) comprises detecting the exogenous label of the crippled DNA polymerase.
7. The method of paragraph 6, wherein the exogenous label of the crippled DNA polymerase comprises a fluorescent moiety, and wherein step (b) comprises measuring a fluorescent signal produced by the fluorescent moiety of the crippled DNA polymerase.
8. The method of any one of paragraphs 1-7, wherein the primer comprises a free 3' hydroxyl moiety.
9. The method of any one of paragraphs 1-8, further comprising, after step (b), the step of replacing the first reaction mixture with a second reaction mixture that comprises a second polymerase and a second type of nucleotide, and then incorporating the second type of nucleotide into the primer of the primed template nucleic acid.
10. The method of paragraph 9, wherein the second type of nucleotide is a reversible terminator nucleotide that comprises a reversible terminator moiety, and wherein incorporation of the reversible terminator nucleotide produces a blocked primed template nucleic acid molecule.
11. The method of paragraph 10, further comprising the step of removing the reversible terminator moiety from the blocked primed template nuclei acid molecule to regenerate the primed template nucleic acid molecule.
12. The method of paragraph 10, further comprising repeating steps (a)-(c) using the blocked primed template nucleic acid molecule in place of the primed template nucleic acid.
13. The method of paragraph 11, further comprising repeating steps (a)-(c).
14. The method of paragraph 1, wherein the polypeptide sequence of the crippled DNA polymerase is either SEQ ID NO:1 with the exception of having amino acid position 381 substituted by glutamate, or SEQ ID NO:1 with the exception of having amino acid position 558 substituted by glutamate.
15. The method of paragraph 1, wherein the polypeptide sequence of the crippled DNA polymerase is either SEQ ID NO:2 with the exception of having amino acid position 364 substituted by glutamate, or SEQ ID NO:2 with the exception of having amino acid position 541 substituted by glutamate.
16. The method of paragraph 1, wherein the polypeptide sequence of the crippled DNA polymerase is either SEQ ID NO:3 with the exception of having amino acid position 355 substituted by glutamate, or SEQ ID NO:3 with the exception of having amino acid position 532 substituted by glutamate.

17. The method of paragraph 1, wherein the first reaction mixture comprises divalent magnesium ion.

18. The method of any one of paragraphs 1-17, wherein the first reaction mixture comprises $Mg^{2+}$ ions, and wherein the primer comprises a 3' hydroxyl moiety.

19. A kit for identifying a next correct nucleotide to be incorporated into a primed template nucleic acid molecule, the kit comprising in packaged combination of one or more containers:
(a) a crippled DNA polymerase that forms a ternary complex with the primed template nucleic acid and the next correct nucleotide, but which is substantially incapable of magnesium-catalyzed phosphodiester bond formation;
(b) four types of deoxyribonucleotide triphosphate molecules; and
(c) four types of reversible terminator nucleotide.

20. The kit of paragraph 19, wherein the four reversible terminator nucleotide are four non-fluorescent reversible terminator nucleotides.

21. The kit of paragraph 19, wherein the crippled DNA polymerase comprises a detectable label.

22. The kit of paragraph 19, wherein at least one of the four types of deoxyribonucleotide triphosphate molecules comprises a detectable label.

23. The kit of paragraph 19, wherein the crippled DNA polymerase catalyzes phosphodiester bond formation in the presence of manganese ions.

24. The kit of paragraph 19, further comprising a chemical reagent that removes reversible terminator moieties from the four types of reversible terminator nucleotide.

25. The kit of paragraph 19, wherein each of the four different types of deoxyribonucleotide triphosphate molecules is incorporable by a DNA polymerase comprising magnesium-dependent polymerase activity.

26. The kit of paragraph 19, further comprising a second DNA polymerase that incorporates the next correct nucleotide into the primed template nucleic acid molecule.

27. The kit of paragraph 26, wherein the second DNA polymerase incorporates one of the four types of reversible terminator nucleotide as the next correct nucleotide.

28. The kit of paragraph 19, further comprising a flow cell.

29. The kit of paragraph 19, wherein the four types of deoxyribonucleotide triphosphate molecules comprise dATP, dGTP, dCTP, and either dTTP or dUTP; and wherein the four types of reversible terminator nucleotides comprise analogs of dATP, dGTP, dCTP, and either dTTP or dUTP, each analog comprising a 3'-$ONH_2$ reversible terminator moiety.

30. The kit of paragraph 19, wherein the crippled DNA polymerase comprises either a polypeptide sequence comprising SEQ ID NO:12, or a polypeptide sequence comprising SEQ ID NO:14.

31. The kit of paragraph 30, wherein the polypeptide sequence comprising SEQ ID NO:12 comprises SEQ ID NO:3 with the exception of having amino acid position 355 substituted by glutamate.

32. The kit of paragraph 30, wherein the polypeptide sequence comprising SEQ ID NO:14 comprises SEQ ID NO:3 with the exception of having amino acid position 532 substituted by glutamate.

33. A mutant DNA polymerase comprising a polypeptide sequence, said polypeptide sequence comprising SEQ ID NO:12,
wherein said mutant DNA polymerase forms ternary complexes with primed template nucleic acid molecules and cognate nucleotides, and
wherein said mutant DNA polymerase is substantially incapable of magnesium-catalyzed phosphodiester bond formation.

34. The mutant DNA polymerase of paragraph 33, wherein the crippled DNA polymerase catalyzes formation of phosphodiester bonds in the presence of divalent manganese ions.

35. The mutant DNA polymerase of paragraph 33, wherein the polypeptide sequence of the mutant DNA polymerase is selected from the group consisting of:
SEQ ID NO:1 with the exception of having amino acid position 381 substituted by glutamate,
SEQ ID NO:2 with the exception of having amino acid position 364 substituted by glutamate, and
SEQ ID NO:3 with the exception of having amino acid position 355 substituted by glutamate.

36. The mutant DNA polymerase of paragraph 35, further comprising a reporter moiety attached thereto.

37. A mutant DNA polymerase comprising a polypeptide sequence, said polypeptide sequence comprising SEQ NO:14,
wherein said mutant DNA polymerase forms ternary complexes with primed template nucleic acid molecules and cognate nucleotides, and
wherein said mutant DNA polymerase is substantially incapable of magnesium-catalyzed phosphodiester bond formation.

38. The mutant DNA polymerase of paragraph 37, wherein the polypeptide sequence of the mutant DNA polymerase is selected from the group consisting of:
SEQ ID NO:1 with the exception of having amino acid position 558 substituted by glutamate,
SEQ ID NO:2 with the exception of having amino acid position 541 substituted by glutamate, and
SEQ ID NO:3 with the exception of having amino acid position 532 substituted by glutamate.

39. The isolated mutant DNA polymerase of paragraph 38, further comprising a reporter moiety attached thereto.

DETAILED DESCRIPTION

The following description relates to a sequencing-by-binding (SBB) technique that relies on use of a mutant, non-catalytic DNA polymerase (a "crippled" polymerase). Crippled DNA polymerase enzymes useful for practicing the technique are substantially unable to catalyze magnesium-dependent formation of a phosphodiester bond between a primer strand of a primed template nucleic acid, and an incoming next correct nucleotide. Although being without this catalytic activity, the mutant enzyme retains the ability to discriminate cognate from non-cognate nucleotides. In some embodiments, the mutant polymerase is unable to bind the divalent cation ordinarily needed for catalytic function. Although the following description exemplifies useful aspects of crippled polymerase in the context of SBB, it will be understood that the polymerase can have other uses including, but not limited to, identifying individual nucleotides in a nucleic acid (e.g., detecting single nucleotide polymorphisms) or binding to particular sequences to provide polymerase-mediated affinity separation of the nucleic acids that bear the sequences. Advantageously, use of crippled DNA polymerases overcome problems associated with undesired incorporation of residual nucleotides that may remain following wash steps, or undesired incorporation resulting from incomplete inhibition that can be achieved using non-catalytic metal ions that inhibit polymerase activity. Thus, use of the crippled DNA polymerase can reduce sequencing artifacts associated with undesired incorporation of nucleotides.

Briefly, formation of a stable complex that includes a primed template nucleic acid, a cognate nucleotide, and a crippled DNA polymerase, can be detected even in the presence of catalytic divalent cations. The primer need not have an extension blocking group and the nucleotide need not have moieties that inhibit incorporation into the primer. After cognate nucleotide for a particular position has been identified, or at least monitoring or measuring information needed to make the identification has been gathered, the primed template nucleic acid can be contacted with a different reaction mixture that includes second DNA polymerase instead of the crippled DNA polymerase. The second DNA polymerase, when further provided with a cognate nucleotide and appropriate divalent cation, will be capable of joining the cognate nucleotide to the primer at the position of a free 3' hydroxyl group. If a reversible terminator nucleotide is employed in this step, then only a single incorporation will occur.

Advantageously, the technique can be practiced using various types of nucleotides, including native (e.g., unlabeled) nucleotides, nucleotides with detectable labels (e.g., fluorescent or other optically detectable labels), or labeled or unlabeled nucleotide analogs (e.g., modified nucleotides containing reversible terminator moieties). Further, the technique provides controlled reaction conditions, unambiguous determination of sequence, low overall cost of reagents, and low instrument cost.

The disclosed technique can be applied to binding reactions used for determining the identity of the next base of a primed template nucleic acid by any means and for any reason. The technique can be used to monitor specific binding of a DNA polymerase and the next correct nucleotide (e.g., a dNTP) complementary to a primed template nucleic acid, and to distinguish specific binding from nonspecific binding. The technique may be applied to single nucleotide determination (e.g., SNP determination), or alternatively to more extensive nucleic acid sequencing procedures employing iterative cycles that identify one nucleotide at a time. For example, the methods provided herein can be used in connection with sequencing-by-binding procedures, as described in the commonly owned U.S. patent application identified by Ser. No. 14/805,381 (published as U.S. Pat. App. Pub. No. 2017/0022553 A1), the disclosure of which is incorporated by reference herein in its entirety.

Definitions

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "sequencing-by-binding" refers to a sequencing technique wherein specific binding of a polymerase to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, "nucleic acid" or "oligonucleotide" or "polynucleotide" or grammatical equivalents used herein means at least two nucleotides covalently linked together. Thus, a "nucleic acid" is a polynucleotide, such as DNA, RNA, or any combination thereof, that can be acted upon by a polymerizing enzyme during nucleic acid synthesis. The term "nucleic acid" includes single-, double-, or multiple-stranded DNA, RNA and analogs (derivatives) thereof. Double-stranded nucleic acids advantageously can minimize secondary structures that may hinder nucleic acid synthesis. A double stranded nucleic acid may possess a nick or a single-stranded gap.

As used herein, a "template nucleic acid" is a nucleic acid to be detected or sequenced using any sequencing method disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, a primed template nucleic acid can have either a 3'-end that is extendible by a polymerase, or a 3'-end that is blocked from extension.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (ribose or deoxyribose), and at least one phosphate group. The term embraces, but is not limited to, ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the sequencing-by-binding procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has one or more modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is modified with a moiety. The moiety may be a 3' reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, the "next template nucleotide" (or the "next template base") refers to the next nucleotide (or base) in a template nucleic acid that is located immediately downstream of the 3'-end of a hybridized primer. In other words, the next template nucleotide is located immediately 5' of the base in the template that is hybridized to the 3' end of the primer.

As used herein, a "blocking moiety," when used with reference to a nucleotide analog, is a part of the nucleotide that inhibits or prevents the nucleotide from forming a covalent linkage to a second nucleotide (e.g., via the 3'-OH of a primer nucleotide) during the incorporation step of a nucleic acid polymerization reaction. The blocking moiety of a "reversible terminator" nucleotide can be removed from the nucleotide analog to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, a "test nucleotide" is a nucleotide being investigated for its ability to participate in formation of a ternary complex that further includes a primed template nucleic acid and a polymerase.

As used herein, "polymerase" is a generic term for a nucleic acid synthesizing enzyme, including but not limited to, DNA polymerase, RNA polymerase, reverse transcriptase, primase and transferase. Typically, the polymerase includes one or more active sites at which nucleotide binding and/or catalysis of nucleotide polymerization may occur. The polymerase may catalyze the polymerization of nucleotides to the 3'-end of a primer bound to its complementary nucleic acid strand. For example, a polymerase can catalyze the addition of a next correct nucleotide to the 3' oxygen of the primer via a phosphodiester bond, thereby chemically incorporating the nucleotide into the primer. Optionally, the polymerase used in the provided methods is a processive polymerase. Optionally, the polymerase used in the provided methods is a distributive polymerase. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, a "salt providing monovalent cation" is an ionic compound that dissociates in aqueous solution to produce cations having a single positive charge. For example, the cations can be metal cations where the oxidation state is +1.

As used herein, "a glutamate salt" is an ionic compound that dissociates in aqueous solution to produce glutamate anions.

As used herein, "biphasic" refers to a two-stage process wherein a primed template nucleic acid is contacted with a polymerase and a test nucleotide. The first phase of the process involves contacting the primed template nucleic acid with a polymerase in the presence of a sub-saturating level of nucleotide(s), or even in the absence of nucleotides. The term "sub-saturating," when used in reference to ligand that binds to a receptor (e.g., a nucleotide that binds to a polymerase), refers to a concentration of the ligand that is below that required to result in at least 90% of the receptors being bound to the ligand at equilibrium. For example, a sub-saturating amount of nucleotide can yield at least 90%, 95%, 99% or more polymerases being bound to the nucleotide. The second phase of the process involves contacting the primed template nucleic acid from the first phase with a polymerase in the presence of a higher concentration of nucleotide(s) than used in the first phase, where the higher concentration is sufficient to yield maximal ternary complex formation when a nucleotide in the reaction is the next correct nucleotide.

As used herein, "providing" a template, a primer, a primed template nucleic acid, or a blocked primed template nucleic acid refers to the preparation and delivery of one or many nucleic acid polymers, for example to a reaction mixture or reaction chamber.

As used herein, "monitoring" (or sometimes "measuring") refers to a process of detecting a measurable interaction or binding between two molecular species. For example, monitoring may involve detecting measurable interactions between a polymerase and primed template nucleic acid, typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting" refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a primed template and nucleotide, refers to the process of joining a cognate nucleotide to a primer by formation of a phosphodiester bond.

As used herein, "extension" refers to the process after an oligonucleotide primer and a template nucleic acid have annealed to one another, wherein a polymerase enzyme catalyzes addition of one or more nucleotides at the 3'-end of the primer. A nucleotide that is added to a nucleic acid by extension is said to be "incorporated" into the nucleic acid. Accordingly, the term "incorporating" can be used to refer to the process of joining a nucleotide to the 3'-end of a primer by formation of a phosphodiester bond.

As used herein, a "binary complex" is an intermolecular association between a polymerase and a primed template nucleic acid (or blocked primed template nucleic acid), where the complex does not include a nucleotide molecule such as the next correct nucleotide.

As used herein, a "ternary complex" is an intermolecular association between a polymerase, a primed template nucleic acid (or blocked primed template nucleic acid), and the next correct nucleotide positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation). The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations necessary to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety that has been added to a sequencing reagent, such as a nucleotide or a polymerase (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a conformationally sensitive fluorescent dye that changes its properties upon nucleotide binding also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, a "native DNA polymerase" is a modified or unmodified DNA polymerase enzyme that possesses the ability to discriminate cognate nucleotide from a non-cognate nucleotide, and to incorporate the cognate nucleotide into the growing primer strand, by forming a phosphodiester bond joining the two species when also provided with a catalytic divalent metal ion (e.g., $Mg^{2+}$ or $Mn^{2+}$).

As used herein, a "crippled DNA polymerase" is a mutated version of a DNA polymerizing enzyme, where the mutant is capable of discriminating the next correct nucleotide from an incorrect nucleotide (e.g., being able to form a template-dependent complex with a primed template nucleic acid and cognate nucleotide), but incapable of catalyzing phosphodiester bond formation between the primer and the cognate nucleotide. For example, one or more amino acid positions of a native DNA polymerase can be modified (e.g., by site-directed mutagenesis of the polynucleotide encoding same and/or by chemical modification of one or more sites in the polynucleotide) to create the crippled DNA polymerase.

As used herein, a "kit" is a packaged unit containing one or more components that can be used for performing detection and/or sequencing reactions using a crippled DNA polymerase, as disclosed herein. Typical kits may include packaged combinations, in one or more containers or vials, of reagents to be used in the procedure.

Sequencing-by-Binding

Described herein are polymerase-based, nucleic acid sequencing-by-binding (SBB) reactions, wherein a crippled DNA polymerase undergoes a conformational transition upon encountering a primed template nucleic acid molecule and the next correct nucleotide. The crippled DNA polymerase is unable to catalyze phosphodiester bond formation, and so lingers in the complex referred to herein as the "ternary" complex. Detection of the ternary complex by any approach is a surrogate for detecting the cognate nucleotide.

The disclosed approach shares many features in common with conventional SBB techniques (disclosed in the commonly owned U.S. patent application identified by Ser. No. 14/805,381), which will be described below in general terms. Of course, any reference to magnesium-based catalysis by the same enzyme used for the examination step do not apply to the crippled DNA polymerase.

In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation including a polymerase, primed template nucleic acid and nucleotide; wherein the bound nucleotide has not been incorporated. This step, also referred to herein as the "examination" step, may be followed by a chemical step wherein a phosphodiester bond is formed with concomitant pyrophosphate cleavage from the nucleotide (i.e., nucleotide incorporation). The polymerase, primed template nucleic acid and newly incorporated nucleotide produce a post-chemistry, pre-translation conformation. As both the pre-chemistry conformation and the pre-translocation conformation include a polymerase, primed template nucleic acid and nucleotide, wherein the polymerase is in a closed state, either conformation may be referred to herein as a closed-complex or a closed ternary complex. In the closed pre-insertion state, divalent catalytic metal ions, such as $Mg^{2+}$ mediate a rapid chemical reaction involving nucleophilic displacement of a pyrophosphate (PPi) by the 3' hydroxyl of the primer. The polymerase returns to an open state upon the release of PPi, the post-translocation step, and translocation initiates the next round of reaction. While a closed-complex can form in the absence of divalent catalytic metal ions (e.g., $Mg^{2+}$), the polymerase of the closed complex is proficient in chemical addition of nucleotide in the presence of the divalent metal ions when provided with an appropriate substrate having an available 3'hydroxyl group. Low or deficient levels of catalytic metal ions, such as $Mg^{2+}$, lead to non-covalent (e.g., physical) sequestration of the next correct nucleotide in a closed-complex. This closed-complex may be referred to as a stabilized or trapped closed-complex. In any reaction step described above, the polymerase configuration and/or interaction with a nucleic acid may be monitored during an examination step to identify the next correct base in the template nucleic acid sequence. Before or after incorporation, reaction conditions can be changed to disengage the polymerase from the primed template nucleic acid, and changed again to remove from the local environment any reagents that inhibit polymerase binding.

Generally speaking, the SBB procedure includes an "examination" step that identifies the next template base, and optionally an "incorporation" step that adds one or more complementary nucleotides to the 3'-end of the primer component of the primed template nucleic acid. Identity of the next correct nucleotide to be added is determined either without, or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) and one or more test nucleotides being investigated as the possible next correct nucleotide. Further, there is a step that involves monitoring or measuring the interaction between the polymerase and the primed template nucleic acid in the presence of the test nucleotides. Optionally, the interaction can take place in the presence of stabilizers, whereby the polymerase-nucleic acid interaction is stabilized in the presence of the next correct nucleotide. Again, the examination step identifies or determines the identity of the next correct nucleotide without requiring incorporation of that nucleotide. Stated differently, identity of the next correct nucleotide can be established without chemical incorporation of the nucleotide into the primer when one or more cycles of examination is carried out using labeled or unlabeled nucleotides.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified. Thus, such sequencing methods are fully disclosed herein.

The Examination Step

An examination step according to the technique described herein typically includes the following substeps: (1) providing a primed template nucleic acid (i.e., a template nucleic acid molecule hybridized with a primer that optionally may be blocked from extension at its 3'-end); (2) contacting the primed template nucleic acid with a reaction mixture that includes a crippled DNA polymerase and at least one nucleotide; (3) monitoring the interaction of the crippled DNA polymerase with the primed template nucleic acid molecule in the presence of the nucleotide(s) and without chemical incorporation of any nucleotide into the primed template nucleic acid; and (4) identifying the next base in the template nucleic acid (i.e., the next correct nucleotide) using the monitored interaction. Optionally, the primed template nucleic acid molecule can be contacted initially with the crippled DNA polymerase in the absence of nucleotide(s) before contacting any nucleotide. The primer of the primed template nucleic acid can be an extendible primer. The primed template nucleic acid, the crippled DNA polymerase and the test nucleotide are capable of forming a ternary complex when the base of the test nucleotide is complementary to the next base of the primed template nucleic acid molecule. The primed template nucleic acid and the crippled DNA polymerase are capable of forming a binary complex when the base of the test nucleotide is not complementary to the next base of the primed template nucleic acid molecule. Optionally, the contacting occurs under conditions that favor formation of the ternary complex over formation of the binary complex. The identifying step can include identifying the base of the nucleotide that is complementary to the next base of the primed template nucleic acid. Optionally, this includes contacting ternary complexes with one or more wash solutions having different nucleotide compositions that permit ternary complexes to be selectively maintained or dissociated.

All of these steps can be repeated one or more times to obtain extensive sequence information. For example, ternary complexes can be formed initially by contacting a primed template nucleic acid (optionally including a blocked 3'-end) with a crippled DNA polymerase (optionally labeled with an exogenous label) and one or more nucleotides (optionally including one or more exogenous labels). Buffer conditions can be changed such that ternary complexes are contacted with a wash solution that includes only a subset of nucleotides used for forming the ternary complex. Optionally, this buffer includes the same crippled DNA polymerase used to form the ternary complex. Monitoring interaction of the crippled DNA polymerase and/or nucleotide in the ternary complex can be carried out to determine whether the ternary complex remains stable (thereby indicating that one of the nucleotides in the wash buffer corresponds to the cognate nucleotide) or becomes destabilized (thereby indicating that the buffer no longer contains the cognate nucleotide). The wash steps can be repeated until the ternary complex becomes destabilized by progressively omitting one nucleotide that was present during the preceding wash cycle. Optionally, a cognate nucleotide can be incorporated by a second DNA polymerase following one or a plurality of reagent exchanges.

All of these steps can be repeated one or more times to obtain extensive sequence information. For example, the contacting and monitoring steps can be repeated one or more times. Optionally, the contacting and monitoring steps are repeated using a reaction mixture that includes the crippled DNA polymerase and a first test nucleotide. Optionally, the contacting and monitoring steps are repeated using a reaction mixture that includes the crippled DNA polymerase and a second nucleotide. Optionally, the contacting and monitoring steps are repeated using a reaction mixture that includes the crippled DNA polymerase and a third nucleotide. Optionally, the contacting and monitoring steps are repeated using a reaction mixture that includes the crippled DNA polymerase and a fourth nucleotide.

In the sequencing methods provided herein, the reaction mixture used for forming ternary complexes, that includes the crippled DNA polymerase and at least one test nucleotide, can include at least 1, 2, 3, or 4 types of nucleotide molecules (e.g., either labeled or unlabeled nucleotides). Alternatively or additionally, the reaction mixture can include at most 4, 3, 2 or 1 types of nucleotide molecules. Optionally, the nucleotides are native nucleotides selected from dATP, dTTP, dCTP, and dGTP. Optionally, the reaction mixture includes one or more triphosphate nucleotides and one or more diphosphate nucleotides. Optionally, a closed-complex is formed between the primed template nucleic acid, the crippled DNA polymerase, and one of four nucleotide molecules included in the reaction mixture.

In a particular example of the provided method, the primed template nucleic acid (optionally blocked at its 3'-end) is contacted with a reaction mixture that includes polymerase with one or more nucleotides. A ternary complex will form if one or more of the nucleotides is a cognate nucleotide for the position being interrogated.

In another particular example of the provided method, the primed template nucleic acid (optionally blocked at its 3'-end) is initially contacted with a reaction mixture that includes the crippled DNA polymerase without added test nucleotide. Thereafter, the primed template nucleic acid is contacted with a reaction mixture that includes the crippled DNA polymerase and one or more test nucleotides that may participate in ternary complex formation. Thereafter, the optionally blocked primed template nucleic acid is contacted with a reaction mixture that includes polymerase and one fewer nucleotide than the preceding reaction mixture. Monitoring maintenance or destabilization of any ternary complex can take place continuously, or after each reaction mixture change.

Since nucleotide incorporation does not take place during the examination step, a separate incorporation step may be performed after determining the identity of the next correct nucleotide, or at least acquiring the results necessary to make the determination. The separate incorporation step may be accomplished without the need for monitoring, as the cognate nucleotide has already been identified during the examination step. A reversibly terminated nucleotide may also be used to prevent the addition of subsequent nucleotides. The SBB method allows for controlled determination of a template nucleic acid base with or without the use of labeled nucleotides, as the interaction between the crippled DNA polymerase and template nucleic acid can be monitored with or without a label on the nucleotide. To be clear, however, the use of a labeled nucleotide (e.g., a fluorescent nucleotide) is optional when performing the presently disclosed procedure to allow for fluorescent detection of bound nucleotide.

In the sequencing methods provided herein, the test nucleotide (e.g., at least one test nucleotide) can include a 3' hydroxyl group, or a blocking moiety that prevents phosphodiester bond formation at the 3'-end of the primer. A 3' terminator moiety or a 2' terminator moiety may be either a reversible terminator or an irreversible terminator. Optionally, the reversible terminator of the at least one nucleotide molecule is replaced or removed at some point after the examination step that employed the test nucleotide that included the reversible terminator.

Contacting Steps

Contacting of the primed template nucleic acid molecule with reaction mixtures that include the crippled DNA polymerase and one or more test nucleotide molecules can occur under conditions that stabilize formation of the ternary complex and/or destabilize formation of the binary complex. Optionally, the reaction mixture includes potassium glutamate. Optionally, the conditions that stabilize formation of the ternary complex include contacting the primed template nucleic acid with a stabilizing agent. Optionally, the reaction mixture includes a stabilizing agent. The stabilizing agent can be one or more non-catalytic metal ions that inhibit polymerase-mediated incorporation. Exemplary non-catalytic metal ions useful for this purpose include strontium ion, tin ion, nickel ion, and europium ion. For example, the reaction mixture of the examination step that includes the primed template nucleic acid, the polymerase, and the test nucleotide also may include from 0.01 mM to 30 mM strontium chloride as a stabilizing agent.

Alternatively, and particularly when using a blocked primed template nucleic acid to form a ternary complex in the examination step, reaction mixtures used for conducting examination and monitoring steps optionally can include catalytic metal ions (e.g., $Mg^{2+}$ or $Mn^{2+}$). Concentrations of the catalytic metal ions needed to support polymerization activity when using unmodified (i.e., not 3' blocked) primers will be familiar to those having an ordinary level of skill in the art.

In certain embodiments, the primed template nucleic acid is immobilized to the surface of a solid support. The immobilization may employ either a covalent or a noncovalent bond between one or the other, or even both strands of the primed template nucleic acid and the solid support. For example, when the template and primer strands of the primed template nucleic acid are different molecules, the template strand can be immobilized, for example via its 5'-end. What is necessary, however, is that the 3' terminus of the primer is available for interacting with the polymerase.

When the primed template nucleic acid is immobilized to a solid support, there are alternatives for how the contacting steps are performed. For example, the solid support can be physically transferred between different vessels (e.g., individual wells of a multiwell plate) containing different reagent solutions. This is conveniently accomplished using an automated or robotic instrument. In another example, the primed template nucleic acid is immobilized to a solid support inside a flow cell or chamber. In this instance, different contacting steps can be executed by controlled flow of different liquid reagents through the chamber, or across the immobilized primed template nucleic acid.

The Monitoring Step

Monitoring or measuring the interaction of the crippled DNA polymerase with the primed template nucleic acid molecule in the presence of a nucleotide molecule may be accomplished in many different ways. For example, monitoring can include measuring association kinetics for the interaction between the primed template nucleic acid, the crippled DNA polymerase, and a nucleotide. Monitoring the interaction of the crippled DNA polymerase with the primed template nucleic acid molecule in the presence of a nucleotide molecule can include measuring equilibrium binding constants between the crippled DNA polymerase and primed template nucleic acid molecule (i.e., equilibrium binding constants of polymerase to the template nucleic acid in the presence of a nucleotide). Thus, for example, the monitoring includes measuring the equilibrium binding constant of the crippled DNA polymerase to the primed template nucleic acid in the presence of a nucleotide. Monitoring the interaction of the crippled DNA polymerase with the primed template nucleic acid molecule in the presence of a nucleotide molecule includes measuring dissociation kinetics of the polymerase from the primed template nucleic acid in the presence of any one of the four nucleotides. Optionally, monitoring the interaction of the crippled DNA polymerase with the primed template nucleic acid molecule in the presence of a nucleotide molecule includes measuring kinetics of the dissociation of the closed-complex (i.e., dissociation of the primed template nucleic acid, the polymerase, and the nucleotide). Optionally, the measured association kinetics differ depending on the identity of the nucleotide molecule. Optionally, the crippled DNA polymerase has a different affinity for each type of nucleotide employed. Optionally, the crippled DNA polymerase has a different dissociation constant for each type of nucleotide in each type of closed-complex. Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135(1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties.

The monitoring step can include monitoring the steady state interaction of the polymerase with the primed template nucleic acid in the presence of a first nucleotide, without chemical incorporation of the first nucleotide into the primer of the primed template nucleic acid. Optionally, monitoring includes monitoring the dissociation of the polymerase from the primed template nucleic acid in the presence of a first nucleotide, without chemical incorporation of the first nucleotide into the primer of the primed template nucleic acid. Optionally, monitoring includes monitoring the association of the polymerase with the primed template nucleic acid in the presence of the first nucleotide, without chemical incorporation of the first nucleotide into the primer of the primed template nucleic acid. Again, test nucleotides in these procedures may be native nucleotides (i.e., unlabeled), labeled nucleotides (e.g., fluorescently labeled nucleotides), or nucleotide analogs (e.g., nucleotides modified to include reversible or irreversible terminator moieties).

Since the crippled DNA polymerase is substantially unable to catalyze phosphodiester bond formation, it is optional to include a catalytic metal ion in the examination reaction mixture. Of course, the absence of a catalytic metal ion in the reaction mixture, or the absence of a catalytic metal ion in the active site of the polymerase prevents the chemical incorporation of the nucleotide into the primer of the primed template nucleic acid.

The examination step may be controlled, in part, by providing reaction conditions to prevent chemical incorporation of a nucleotide while allowing monitoring of the interaction between the crippled DNA polymerase and the primed template nucleic acid, thereby permitting determination of the identity of the next base of the nucleic acid template strand. Such reaction conditions may be referred to as "examination reaction conditions." Optionally, a ternary complex or closed-complex is formed under examination conditions. Optionally, a stabilized ternary complex or closed-complex is formed under examination conditions or in a pre-chemistry conformation. Optionally, a stabilized closed-complex is in a pre-translocation conformation, wherein the enclosed nucleotide has been incorporated, but the closed-complex does not allow for the incorporation of a subsequent nucleotide. Optionally, the examination conditions accentuate the difference in affinity for polymerase to primed template nucleic acids in the presence of different nucleotides. Optionally, the examination conditions cause differential affinity of the crippled DNA polymerase for the primed template nucleic acid in the presence of different nucleotides. By way of example, the examination conditions that cause differential affinity of the crippled DNA polymerase for the primed template nucleic acid in the presence of different nucleotides include, but are not limited to, high salt and inclusion of potassium glutamate. Concentrations of potassium glutamate that can be used to alter polymerase affinity for the primed template nucleic acid include 10 mM to 1.6 M of potassium glutamate, or any amount in between 10 mM and 1.6 M. Optionally, high salt refers to a concentration of salt from 50 mM to 1,500 mM salt.

Examination typically involves, in the monitoring step, detecting crippled DNA polymerase interaction with a template nucleic acid, or with template nucleic acid and nucleotide in combination. Detection may include optical, electrical, thermal, acoustic, chemical and mechanical means. Optionally, monitoring is performed after a buffer change or a wash step, wherein the wash step removes any non-bound reagents (e.g., unbound polymerases and/or nucleotides) from the region of observation. Optionally, monitoring is performed during a buffer change or a wash step, such that the dissociation kinetics of the polymerase-nucleic acid or polymerase-nucleic acid-nucleotide complexes may be used to determine the identity of the next base. Optionally, monitoring is performed during the course of addition of the examination reaction mixture or first reaction mixture, such that the association kinetics of the polymerase to the nucleic acid may be used to determine the identity of the next base on the nucleic acid. Optionally, monitoring involves distinguishing closed-complexes from binary complexes of polymerase and primed template nucleic acid. Optionally, monitoring is performed under equilibrium conditions where the affinities measured are equilibrium affinities. Multiple examination steps including different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination.

In an exemplary sequencing reaction, the examination step includes formation and/or stabilization of a closed-complex including a crippled DNA polymerase, a primed template nucleic acid, and the next correct nucleotide. Characteristics of the formation and/or release of the closed-complex are monitored to identify the enclosed nucleotide and therefore the next base in the template nucleic acid. Closed-complex characteristics can be dependent on the sequencing reaction components (e.g., crippled DNA polymerase, primer, template nucleic acid, nucleotide) and/or reaction mixture components and/or conditions. Optionally, the closed-complex is in a pre-chemistry conformation. Optionally, the closed-complex is in a pre-translocation conformation. Optionally, the closed-complex is in a post-translocation conformation.

The examination step involves monitoring the interaction of a crippled DNA polymerase with a primed template nucleic acid in the presence of a test nucleotide. The formation of a closed-complex may be monitored. Optionally, the absence of formation of a closed-complex is monitored. Optionally, the dissociation of a closed-complex is monitored. Optionally, the incorporation step involves monitoring incorporation of a nucleotide. Optionally, the incorporation step involves monitoring the absence of nucleotide incorporation.

Any process of the examination and/or incorporation step may be monitored. Optionally, a crippled DNA polymerase has an exogenous label or "tag." Optionally, the detectable tag or label on the crippled DNA polymerase is removable. Optionally, the nucleotides or crippled DNA polymerases have a detectable label, however, the label is not detected during sequencing. Optionally, no component of the sequencing reaction is detectably labeled with an exogenous label.

Monitoring the variation in affinity of a crippled DNA polymerase for a template nucleic acid in the presence of correct and incorrect nucleotides, under conditions that do not allow the incorporation of the nucleotide, may be used to determine the sequence of the nucleic acid. The affinity of a crippled DNA polymerase for a template nucleic acid in the presence of different nucleotides, including modified or labeled nucleotides, can be monitored as the off-rate of the polymerase-nucleic acid interaction in the presence of the various nucleotides. The affinities and off-rates of many standard polymerases to various matched/correct, mismatched/incorrect and modified nucleotides are known in the art. Single molecule imaging of Klenow polymerase reveals that the off-rate for a template nucleic acid for different nucleotide types, where the nucleotide types are prevented from incorporating, are distinctly and measurably different.

Optionally, a nucleotide of a particular type is made available to a crippled DNA polymerase in the presence of a primed template nucleic acid. The reaction is monitored, wherein, if the nucleotide is a next correct nucleotide, the polymerase may be stabilized to form a closed-complex. If the nucleotide is an incorrect nucleotide, a closed-complex may still be formed; however, without the additional assistance of stabilizing agents or reaction conditions (e.g., absence of catalytic ions, polymerase inhibitors, salt), the closed-complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the closed-complex. For example, if the next base in the template nucleic acid downstream of the 3'-end of the primer is G, the polymerase-nucleic acid affinity, measured as an off-rate, is expected to be different based on whether dATP, dCTP, dGTP or dTTP are added. In this case, dCTP would have the slowest off-rate, with the other nucleotides providing different off-rates for the interaction. Optionally, the off-rate may be different depending on the reaction conditions, for example, the presence of stabilizing agents (e.g., inhibitory compounds) or reaction conditions (e.g., nucleotide modifications or modified polymerases). Once the identity of the next correct nucleotide is determined, 1, 2, 3, 4 or more nucleotide types may be introduced simultaneously to the reaction mixture under conditions that specifically target the formation of a closed-complex. Excess nucleotides may be removed from the reaction mixture and the reaction conditions modulated (e.g., by use of reversible terminator nucleotides) to incorporate the next correct nucleotide of the closed-complex. This sequencing reaction ensures that only one nucleotide is incorporated per sequencing cycle.

The affinity of a crippled DNA polymerase for a template nucleic acid in the presence of a nucleotide can be measured in a plurality of methods known to one of skill in the art. Optionally, the affinity is measured as an off-rate, where the off-rate is measured by monitoring the release of the crippled DNA polymerase from the template nucleic acid as the reaction is washed by a wash buffer. The polymerase binding rates may be diffusion limited at sufficiently low concentrations of crippled DNA polymerase, wherein if the crippled DNA polymerase falls off from the DNA-polymerase complex, it does not load back immediately, allowing for sufficient time to detect that the polymerase has been released from the complex. For a higher affinity interaction, the crippled DNA polymerase is released from the nucleic acid slowly, whereas a low affinity interaction results in the polymerase being released more rapidly. The spectrum of affinities, in this case, translates to different off-rates, with the off-rates measured under dynamic wash conditions or at equilibrium. The smallest off-rate corresponds to the base complementary to the added nucleotide, while the other off-rates vary, in a known fashion, depending on the combination of crippled DNA polymerase and nucleotide selected.

Optionally, the off-rate is measured as an equilibrium signal intensity after the crippled DNA polymerase and nucleotide are provided in the reaction mixture, wherein the interaction with the lowest off-rate (highest affinity) nucleotide produces the strongest signal, while the interactions with other, varying, off-rate nucleotides produce signals of measurably different intensities. As a non-limiting example, a fluorescently labeled polymerase, measured, preferably, under total internal reflection (TIRF) conditions, produces different measured fluorescence intensities depending on the number of polymerase molecules bound to surface-immobilized nucleic acid molecules in a suitably chosen window of time. The intrinsic fluorescence of the polymerase, for instance, tryptophan fluorescence, may also be utilized. A high off-rate interaction produces low measured intensities, as the number of bound crippled DNA polymerase molecules, in the chosen time window is very small, wherein a high off-rate indicates that most of the polymerase is unbound from the nucleic acid. Any surface localized measurement scheme may be employed including, but not limited to, labeled or fluorescence schemes. Suitable measurement schemes that measure affinities under equilibrium conditions include, but are not limited to, bound mass, refractive index, surface charge, dielectric constant, and other schemes known in the art. Optionally, a combination of on-rate and off-rate engineering yields higher fidelity detection in the proposed schemes. As a non-limiting example, a uniformly low on-rate, base-dependent, varying off-rate results in an unbound polymerase remaining unbound for prolonged periods, allowing enhanced discrimination of the variation in off-rate and measured intensity. The on-rate may be manipulated by lowering the concentration of the added crippled DNA polymerase, nucleotide, or both polymerase and nucleotide.

Optionally, the interaction between the crippled DNA polymerase and the nucleic acid is monitored via a detectable tag attached to the polymerase. The tag may be monitored by detection methods including, but limited to, optical, electrical, thermal, mass, size, charge, vibration, and pressure. The label may be magnetic, fluorescent or charged. For external and internal label schemes, fluorescence anisotropy may be used to determine the stable binding of a crippled DNA polymerase to a nucleic acid in a closed-complex.

By way of example, a crippled DNA polymerase is tagged with a fluorophore, wherein closed-complex formation is monitored as a stable fluorescent signal. The unstable interaction of the crippled DNA polymerase with the template nucleic acid in the presence of an incorrect nucleotide results in a measurably weaker signal compared to the closed-complex formed in the presence of the next correct nucleotide. In certain preferred embodiments, however, the sequencing-by-binding procedure does not rely on detection of any exogenous label (e.g., a fluorescent label) joined to the crippled DNA polymerase.

Optionally, a primed template nucleic acid molecule (optionally blocked at its 3'-end) is contacted with a crippled DNA polymerase and one or more exogenously labeled nucleotides during the examination step. Monitoring of signal generated as a consequence of the presence of the labeled nucleotide provides information concerning formation and stabilization/destabilization of the ternary complex that includes the labeled nucleotide. For example, if the exogenous label is a fluorescent label, and if the primed template nucleic acid is immobilized to a solid support at a particular locus, then monitoring fluorescent signal associated with that locus can be used for monitoring ternary complex formation and stability under different reaction mixture conditions.

The Identifying Step

The identity of the next correct base or nucleotide can be determined by monitoring the presence, formation and/or dissociation of the ternary complex or closed-complex. The identity of the next base may be determined without chemically incorporating the next correct nucleotide into the 3'-end of the primer. Optionally, the identity of the next base is determined by monitoring the affinity of the crippled DNA polymerase for the primed template nucleic acid in the presence of added nucleotides. Optionally, the affinity of the polymerase for the primed template nucleic acid in the presence of the next correct nucleotide may be used to determine the next correct base on the template nucleic acid. Optionally, the affinity of the crippled DNA polymerase for the primed template nucleic acid in the presence of an incorrect nucleotide may be used to determine the next correct base on the template nucleic acid.

In certain embodiments, a ternary complex that includes a primed template nucleic acid (or a blocked primed template nucleic acid) is formed in the presence of a crippled DNA polymerase and a plurality of nucleotides. Cognate nucleotide participating in the ternary complex optionally is identified by observing loss of the complex that occurs when the cognate nucleotide is withdrawn from the reaction mixture, for example by exchanging one reaction mixture for another. Here, destabilization of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide.

The Incorporation Step

Optionally, the methods provided herein further include an incorporation step. By way of example, the incorporation step includes incorporating a single nucleotide (e.g., an unlabeled nucleotide, a reversible terminator nucleotide, or a detectably labeled nucleotide analog) complementary to the next base of the template nucleic acid into the primer of the primed template nucleic acid molecule. Optionally, the incorporation step includes contacting the primed template nucleic acid molecule, polymerase (other than the crippled DNA polymerase used in the examination step) and nucleotide with an incorporation reaction mixture. The incorporation reaction mixture, typically includes a catalytic metal ion.

The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; salt or buffer composition changes, an optical stimulation or a combination thereof. Optionally, the wash step includes contacting the primed template nucleic acid or the primed template nucleic acid/polymerase complex with one or more buffers, detergents, protein denaturants, proteases, oxidizing agents, reducing agents, or other agents capable of releasing internal crosslinks within a polymerase or crosslinks between a polymerase and nucleic acid.

Optionally, the method further includes repeating the examination step and the incorporation step to sequence a template nucleic acid molecule. The examination step may be repeated one or more times prior to performing the incorporation step. Optionally, two consecutive examination steps include reaction mixtures with different nucleotide molecules (e.g., different nucleotides that are labeled or unlabeled). Optionally, prior to incorporating the single nucleotide into the primed template nucleic acid molecule, the first reaction mixture is replaced with a second reaction mixture including a polymerase capable of phosphodiester bond formation and 1, 2, 3, or 4 types of nucleotide molecules (e.g., different unlabeled nucleotides). Optionally, the nucleotide molecules are native nucleotides selected from dATP, dTTP, dCTP, and dGTP.

The incorporation reaction may be enabled by an incorporation reaction mixture. Optionally, the incorporation reaction mixture includes a different composition of nucleotides than the examination reaction. For example, the examination reaction includes one type of nucleotide and the incorporation reaction includes another type of nucleotide. By way of another example, the examination reaction includes one type of nucleotide and the incorporation reaction includes four types of nucleotides, or vice versa. Optionally, the examination reaction mixture is altered or replaced by the incorporation reaction mixture. Optionally, the incorporation reaction mixture includes a catalytic metal ion, potassium chloride, or a combination thereof.

Optionally, the incorporation step includes replacing a nucleotide from the examination step and incorporating another nucleotide into the 3'-end of the template nucleic acid primer. The incorporation step can further involve releasing a nucleotide from within a closed-complex (e.g., the nucleotide is a modified nucleotide or nucleotide analog) and incorporating a nucleotide of a different kind to the 3'-end of the template nucleic acid primer. Optionally, the released nucleotide is removed and replaced with an incorporation reaction mixture including a next correct nucleotide.

Suitable reaction conditions for incorporation may involve replacing the examination reaction mixture with an incorporation reaction mixture. Optionally, nucleotides present in the examination reaction mixture are replaced with one or more nucleotides in the incorporation reaction mixture. Optionally, the polymerase present during the examination step is replaced during the incorporation step. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof. The reagents in the reaction mixture including any combination of polymerase, primed template nucleic acid, and nucleotide may be modified during the examination step and/or incorporation step.

Optionally, the reaction mixture of the incorporation step includes competitive inhibitors, wherein the competitive inhibitors reduce the occurrence of multiple incorporations. In certain embodiments, the competitive inhibitor is a non-incorporable nucleotide. In certain embodiments, the competitive inhibitor is an aminoglycoside. The competitive inhibitor is capable of replacing either the nucleotide or the catalytic metal ion in the active site, such that after the first incorporation the competitive inhibitor occupies the active site preventing a second incorporation. In some embodiments, both an incorporable nucleotide and a competitive inhibitor are introduced in the incorporation step, such that the ratio of the incorporable nucleotide and the inhibitor can be adjusted to ensure incorporation of a single nucleotide at the 3'-end of the primer.

Optionally, the provided reaction mixtures, including the incorporation reaction mixtures, include at least one unlabeled nucleotide molecule that is a non-incorporable nucleotide. In other words, the provided reaction mixtures can include one or more unlabeled nucleotide molecules that are incapable of incorporation into the primer of the primed template nucleic acid molecule. Nucleotides incapable of incorporation include, for example, diphosphate nucleotides. For instance, the nucleotide may contain modifications to the triphosphate group that make the nucleotide non-incorporable. Examples of non-incorporable nucleotides may be found in U.S. Pat. No. 7,482,120, the disclosure of which is incorporated by reference herein in its entirety. Optionally, the primer may not contain a free hydroxyl group at its 3'-end, thereby rendering the primer incapable of incorporating any nucleotide, and, thus making any nucleotide non-incorporable.

A polymerase inhibitor optionally may be included with the reaction mixtures containing test nucleotides in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic-ion binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

In the provided sequencing methods, the next correct nucleotide is identified before the incorporation step, allowing the incorporation step to not require labeled reagents and/or monitoring. Thus, in the provided methods, a nucleotide, optionally, does not contain an attached detectable tag or label. Optionally, the nucleotide contains a detectable label, but the label is not detected in the method. Optionally, the correct nucleotide does not contain a detectable label; however, an incorrect or non-complementary nucleotide to the next base contains a detectable label.

The examination step of the sequencing reaction may be repeated 1, 2, 3, 4 or more times prior to the incorporation step. The examination and incorporation steps may be repeated until the desired sequence of the template nucleic acid is obtained.

Reaction Mixtures

Nucleic acid sequencing reaction mixtures, or simply "reaction mixtures," typically include reagents that are commonly present in polymerase-based nucleic acid synthesis reactions. Reaction mixture reagents include, but are not limited to, enzymes (e.g., the crippled DNA polymerase, or the polymerase used in the incorporation step), dNTPs, template nucleic acids, primer nucleic acids, salts, buffers, small molecules, co-factors, metals, and ions. The ions may be catalytic ions, divalent catalytic ions, non-catalytic ions, non-covalent metal ions, or a combination thereof. The reaction mixture can include salts such as NaCl, KCl, potassium acetate, ammonium acetate, potassium glutamate, $NH_4Cl$, or $NH_4HSO_4$. The reaction mixture can include a source of ions, such as $Mg^{2+}$ or $Mn^+$ Mg-acetate, $Co^+$ or $Ba^{2+}$. The reaction mixture can include tin ions, $Ca^{2+}$, $Zn^{2+}$, $Cu^{2+}$, $Co^{2+}$, $Fe^{2+}$, $Ni^{2+}$, or $Eu^{+3}$. The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are reaction mixtures, optionally, used during the examination step, as well as incorporation reaction mixtures used during nucleotide incorporation that can include one or more of the aforementioned agents. Reaction mixtures, when used during examination, can be referred to herein as examination reaction mixtures. Optionally, the examination reaction mixture includes a high concentration of salt; a high pH; 1, 2, 3, 4, or more types of unlabeled nucleotides; potassium glutamate; a chelating agent; a polymerase inhibitor; a catalytic metal ion; a non-catalytic metal ion that inhibits polymerase-mediated incorporation; or any combination thereof. The examination reaction mixture can include 10 mM to 1.6 M of potassium glutamate or any amount in between 10 mM and 1.6 M. Optionally, the incorporation reaction mixture includes a catalytic metal ion; 1, 2, 3, 4, or more types of nucleotides (e.g., unlabeled nucleotides); potassium chloride; a non-catalytic metal ion that inhibits polymerase-mediated incorporation; or any combination thereof.

Optionally, reaction mixtures in accordance with the disclosed techniques modulate the formation and stabilization of a closed-complex during an examination step. For example, the reaction conditions of the examination step optionally can favor the formation and/or stabilization of a closed-complex encapsulating a nucleotide, and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 mM to 1,500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a closed ternary complex and destabilization of a binary complex. By way of example, the pH of the examination reaction mixture can be adjusted from pH 4.0 to pH 10.0 to favor the stabilization of a closed ternary complex and destabilization of a binary complex. Optionally, the pH of the examination reaction mixture is from pH 4.0 to pH 6.0. Optionally, the pH of the examination reaction mixture is pH 6.0 to pH 10.0.

The provided reaction mixtures and sequencing methods disclosed herein encourage polymerase interaction with the nucleotides and template nucleic acid in a manner that reveals the identity of the next base while controlling the chemical addition of a nucleotide. Optionally, the methods are performed in the absence of detectably labeled nucleotides or in the presence of labeled nucleotides wherein the labels are not detected. Optionally, the reaction mixtures include nucleotides that harbor an exogenous detectable label (e.g., a fluorescent label). Optionally, a plurality of nucleotides in a reaction mixture harbor the same exogenous detectable label. Optionally, a plurality of nucleotides in a reaction mixture harbor different exogenous detectable labels. Optionally, the reaction mixtures can include one or more exogenously labeled polymerase enzymes.

Provided herein are reaction mixtures and methods that facilitate formation and/or stabilization of a closed-complex that includes a polymerase bound to a primed template nucleic acid and a nucleotide enclosed within the polymerase-template nucleic acid complex, under examination reaction mixture conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and subsequent nucleotide incorporation is inhibited. In this instance, the complex is stabilized or trapped in a pre-translocation conformation. For the sequencing reactions provided herein, the closed-complex is stabilized during the examination step, allowing for controlled nucleotide incorporation. Optionally, a stabilized closed-complex is a complex wherein incorporation of an enclosed nucleotide is attenuated, either transiently (e.g., to examine the complex and then incorporate the nucleotide) or permanently (e.g., for examination only) during an examination step. Optionally, a stabilized closed-complex allows for the incorporation of the enclosed nucleotide, but does not allow for the incorporation of a subsequent nucleotide. Optionally, the closed-complex is stabilized in order to monitor any polymerase interaction with a template nucleic acid in the presence of a nucleotide for identification of the next base in the template nucleic acid.

Optionally, the enclosed nucleotide has severely reduced or disabled binding to the template nucleic acid in the closed-complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the closed-complex.

Optionally, the enclosed nucleotide is bound to the polymerase of the closed-complex. Optionally, the enclosed nucleotide is weakly associated with the polymerase of the closed-complex. Optionally, the identity of the polymerase, nucleotide, primer, template nucleic acid, or any combination thereof, affects the interaction between the enclosed nucleotide and the polymerase in the closed-complex. For a given polymerase, each nucleotide has a different affinity for the polymerase than another nucleotide. Optionally, this affinity is dependent, in part, on the template nucleic acid and/or the primer.

The closed-complex may be transiently formed. Optionally, the enclosed nucleotide is a next correct nucleotide. In some methods, the presence of the next correct nucleotide contributes, in part, to the stabilization of a closed-complex. Optionally, the enclosed nucleotide is not a next correct nucleotide.

Optionally, the examination reaction condition comprises a plurality of primed template nucleic acids, polymerases, nucleotides, or any combination thereof. Optionally, the plurality of nucleotides comprises 1, 2, 3, 4, or more types of different nucleotides, for example dATP, dTTP, dGTP, and dCTP. Optionally, the plurality of template nucleic acids is a clonal population of template nucleic acids.

Reaction conditions that may modulate the stability of a closed-complex include, but are not limited to, the availability of catalytic metal ions, suboptimal or inhibitory metal ions, ionic strength, pH, temperature, polymerase inhibitors, cross-linking reagents, and any combination thereof. Reaction reagents which may modulate the stability of a closed-complex include, but are not limited to, non-incorporable nucleotides, incorrect nucleotides, nucleotide analogs, modified polymerases, template nucleic acids with non-extendible polymerization initiation sites, and any combination thereof.

The examination reaction mixture can include other molecules including, but not limited to, enzymes. Optionally, the examination reaction mixture includes any reagents or biomolecules generally present in a nucleic acid polymerization reaction. Reaction components may include, but are not limited to, salts, buffers, small molecules, metals, and ions.

Optionally, properties of the reaction mixture may be manipulated, for example, electrically, magnetically, and/or with vibration.

Nucleotides and Nucleotide Analogs

Nucleotides useful for carrying out the sequencing-by-binding procedures described herein include native nucleotides, labeled nucleotides (e.g., nucleotides that include an exogenous fluorescent dye or other label not found in native nucleotides), and nucleotide analogs (e.g., nucleotides having a reversible terminator moiety).

There is flexibility in the nature of the nucleotides that may be employed in connection with the presently described technique. A nucleotide may include as its nitrogenous base any of: adenine, cytosine, guanine, thymine, or uracil. Optionally, a nucleotide includes inosine, xanthanine, hypoxanthanine, isocytosine, isoguanine, nitropyrrole (including 3-nitropyrrole) or nitroindole (including 5-nitroindole) base. Useful nucleotides include, but are not limited to, ATP, UTP, CTP, GTP, ADP, UDP, CDP, GDP, AMP, UMP, CMP, GMP, dATP, dTTP, dCTP, dGTP, dUTP, dADP, dTDP, dCDP, dGDP, dUDP, dAMP, dTMP, dCMP, dGMP, and dUMP. Optionally, the phosphate group is modified with a moiety. The moiety may include a detectable label. Optionally, the 3' OH group of the nucleotide is modified with a moiety, where the moiety may be a 3' reversible or irreversible terminator moiety. Optionally, the 2' position of the nucleotide is modified with a moiety, where the moiety may be a 2' reversible or irreversible terminator moiety. Optionally, the base of the nucleotide is modified to include a reversible terminator moiety. Nucleotides may also contain terminating inhibitors of DNA polymerase, dideoxynucleotides or 2',3' dideoxynucleotides, which are abbreviated as ddNTPs (ddGTP, ddATP, ddTTP, ddCTP, and ddUTP).

Optionally, a closed-complex of an examination step includes a nucleotide analog or modified nucleotide to facilitate stabilization of the closed-complex. Optionally, a nucleotide analog includes a nitrogenous base, five-carbon sugar, and phosphate group and any component of the nucleotide may be modified and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent nucleotide incorporation to the 3'-end of the primer. One type of reversible terminator is a 3'-O-blocked reversible terminator. The terminator is linked to the oxygen atom of the 3' OH end of the 5-carbon sugar of a nucleotide. Another type of reversible terminator is a 3'-unblocked reversible terminator. The terminator is linked to the nitrogenous base of a nucleotide. For reviews of nucleotide analogs having terminators, see, e.g., Mu, R., et al., "The History and Advances of Reversible Terminators Used in New Generations of Sequencing Technology," Genomics, Proteomics & Bioinformatics 11(1):34-40 (2013), which is incorporated by reference herein in its entirety.

Optionally, nucleotides are substituted for modified nucleotide analogs having terminators that irreversibly prevent nucleotide incorporation to the 3'-end of the primer. Irreversible nucleotide analogs include dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides include a blocking moiety that inhibits or prevents the nucleotide from forming a covalent linkage to a second nucleotide (3' OH of a primer) during the incorporation step of a nucleic acid polymerization reaction. The blocking moiety can be removed from the nucleotide, allowing for nucleotide incorporation.

Optionally, a nucleotide analog present in a closed-complex renders the closed-complex stable. Optionally, the nucleotide analog is non-incorporable. Optionally, the nucleotide analog is released and a native nucleotide is incorporated. Optionally, the closed-complex is released, the nucleotide analog is modified, and the modified nucleotide analog is incorporated. Optionally, the closed-complex is released under reaction conditions that modify and/or destabilize the nucleotide analog in the closed-complex.

Optionally, a nucleotide analog present in a closed-complex is incorporated and the closed-complex is stabilized. The closed-complex may be stabilized by the nucleotide analog, or for example, by any stabilizing methods disclosed herein. Optionally, the nucleotide analog does not allow for the incorporation of a subsequent nucleotide. The closed-complex can be released, for example, by any methods described herein, and the nucleotide analog is modified. The modified nucleotide analog may allow for subsequent incorporation of a nucleotide to its 3'-end.

Optionally, a nucleotide analog is present in the reaction mixture during the examination step. For example, 1, 2, 3, 4 or more nucleotide analogs are present in the reaction mixture during the examination step. Optionally, a nucleotide analog is replaced, diluted, or sequestered during an incorporation step. Optionally, a nucleotide analog is replaced with a native nucleotide. The native nucleotide may include a next correct nucleotide. Optionally, a nucleotide analog is modified during an incorporation step. The modified nucleotide analog can be similar to or the same as a native nucleotide.

Optionally, a nucleotide analog has a different binding affinity for a crippled DNA polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

Optionally, a nucleotide analog is a nucleotide, modified or native, fused to a polymerase. Optionally, a plurality of nucleotide analogs includes fusions to a plurality of polymerases, wherein each nucleotide analog includes a different polymerase.

A nucleotide can be modified to favor the formation of a closed-complex over the formation of a binary complex. A nucleotide may be selected or modified to have a high affinity for a crippled DNA polymerase, wherein the polymerase binds to a nucleotide prior to binding to the template nucleic acid.

Any nucleotide modification that traps the crippled DNA polymerase in a closed-complex may be used in the methods disclosed herein. The nucleotide may be trapped permanently or transiently. Optionally, the nucleotide analog is not the means by which a closed-complex is stabilized. Any closed-complex stabilization method may be combined in a reaction utilizing a nucleotide analog.

Optionally, a nucleotide analog that allows for the stabilization of a closed-complex is combined with reaction conditions that usually release the closed-complex. The conditions include, but are not limited to, the presence of a release reagent (e.g., catalytic metal ion, such as magnesium or manganese). Optionally, the closed-complex is stabilized even in the presence of a catalytic metal ion. Optionally, the closed-complex is released even in the presence of a nucleotide analog. Optionally, the stabilization of the closed-complex is dependent, in part, on the concentrations and/or identity of the stabilization reagent and/or release reagents, and any combination thereof. Optionally, the stabilization of a closed-complex using nucleotide analogs is combined with additional reaction conditions that function to stabilize a closed-complex, including, but not limited to, sequestering, removing, reducing, omitting, and/or chelating a catalytic metal ion; the presence of a polymerase inhibitor, cross-linking agent; and any combination thereof.

Optionally, one or more nucleotides can be labeled with distinguishing and/or detectable tags or labels; however, such tags or labels are not detected during examination, identification of the base or incorporation of the base, and are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase position of the nucleotide. Under suitable reaction conditions, the tagged nucleotides may be enclosed in a closed-complex with the polymerase and the primed template nucleic acid. Alternatively, a tag is attached to the gamma phosphate position of the nucleotide.

Polymerases

Crippled DNA polymerases useful for carrying out the disclosed sequencing-by-binding technique include modified variants of naturally occurring polymerases, including, but not limited to, mutants, recombinants, fusions, genetic modifications, chemical modifications, synthetics, and analogs. Optionally, the modified variants have special properties that enhance their ability to sequence DNA, including enhanced binding affinity to nucleic acids, reduced binding affinity to nucleic acids, enhanced catalysis rates, reduced catalysis rates etc. Mutant polymerases include polymerases wherein one or more amino acids are replaced with other amino acids (naturally or non-naturally occurring), one or more amino acids are chemically modified, and/or one or more amino acids are inserted or deleted. Modified polymerases include polymerases that contain an external tag, which can be used to monitor the presence and interactions of the polymerase. Optionally, intrinsic signals from the polymerase can be used to monitor their presence and interactions. Thus, the provided methods can include monitoring the interaction of the polymerase, nucleotide and template nucleic acid through detection of an intrinsic signal from the polymerase. Optionally, the intrinsic signal is a light scattering signal. For example, intrinsic signals include native fluorescence of certain amino acids such as tryptophan, wherein changes in intrinsic signals from the polymerase may indicate the formation of a closed-complex. Thus, in the provided methods, the polymerase can be an unlabeled polymerase, and monitoring can be performed in the absence of a detectable label associated with the polymerase.

The term polymerase and its variants, as used herein, also refers to fusion proteins including at least two portions linked to each other, for example, where one portion includes a polypeptide that can catalyze the polymerization of nucleotides into a nucleic acid strand is linked to another portion that includes a second moiety, such as, a reporter enzyme or a processivity-modifying domain. For example, T7 DNA polymerase includes a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, including the movement of the thumb and/or finger domains, during the synthesis of nucleic acids.

DNA polymerases that may be modified to yield crippled DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Terminator DNA polymerase from New England BioLabs Inc.; Ipswich, MA) can be used. Still other useful DNA polymerases, including the 3PDX polymerase are disclosed in U.S. Pat. No. 8,703, 461, the disclosure of which is incorporated by reference in its entirety.

RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerases.

Reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and telomerase reverse transcriptase that maintains the telomeres of eukaryotic chromosomes.

Modeling Catalytically Inactive Polymerase Mutants

Described below are the preparation of DNA polymerase I (pol I) large fragment mutants from a thermostable family strain of *Bacillus stearothermophilus* (Bst-f), where the mutants properly form ternary complexes with cognate nucleotides, but are incapable of incorporating those nucleotides in the presence of $Mg^{2+}$ ions. The Bst-f enzyme is a family A polymerase having homology to other well-characterized, high fidelity polymerases, including *E. coli* DNA pol I (KF), *T. aquaticus* DNA pol I (Taq), and *Bacillus subtilis* DNA pol I (Bsu-f). These polymerases share conserved protein sequence motifs needed to fulfill distinct functions, including nucleotide binding and polymerization.

Further, the family A polymerases share common structural architectures known as the fingers, thumb and palm subdomains. The palm subdomain is highly conserved among DNA polymerases, as it includes the catalytic core that will be familiar to those having an ordinary level of skill in the art. The palm also contains catalytic carboxylates from motifs A and C. The conserved acidic amino acid residues, aspartic acid (D) and glutamic acid (E), in motifs A and C are thought to serve as metal ligands for divalent cations during phosphoryl transfer reaction catalyzed by polymerases. Motif A contains a strictly-conserved aspartate at the junction of a beta-strand and an alpha-helix, and motif C has a doublet of negative charges, located in a beta-turn-beta secondary structure.

The parent enzyme ("CBT") used for preparing mutants was an engineered version of the Bst polymerase that had been optimized with respect to cysteine content, and N-terminal sequences that facilitated protein purification and processing. More specifically, the polypeptide sequence identified as SEQ ID NO:1 included a modified N-terminus having: (1) an engineered "His-tag" motif at positions 5-10; (2) a thrombin cleavage site between positions 17 and 18; and (3) a cysteine residue at position 23. The naturally occurring Bst polymerase sequence extended from position 27 to the C-terminus (subject to removal of naturally occurring cysteine residues). It is to be understood that engineered polymerases in accordance with the disclosure optionally include or omit the above-described N-terminal modifications. For example, useful polymerases can be constructed on a parent scaffold of SEQ ID NO:2 (omits sequences upstream of the thrombin cleavage site) or SEQ ID NO:3 (omits sequences upstream of the first amino acid of the native Bst polymerase). Thus, useful modifications that affect capacity for phosphodiester bond formation can be understood with reference to these protein sequence scaffolds.

Arrangements of the conventional A and C motifs are presented below. Both alignments were prepared using standard polypeptide sequence alignment software tools. The underlined and bolded aspartic acid (D) residue in motif A corresponds to amino acid position 653 in the crystal structure of the Bst polymerase (UniProt No. P52026, Protein Data Bank No. 3EZ5). The underlined and bolded aspartic acid and glutamic acid (DE) residues in motif C correspond to amino acid positions 830-831 in the crystal structure of the Bst polymerase (UniProt No. P52026, Protein Data Bank No. 3EZ5).

Motif A

Klenow Fragment
(SEQ ID NO: 4)
DYVIVSADYSQIELRIMAHLSRDKGL

Taq
(SEQ ID NO: 5)
GWLLVALDYSQIELRVLAHLSGDENL

Bst-f
(SEQ ID NO: 6)
DWLIFAADYSQIELRVLAHIAEDDNL

Bsu-f
(SEQ ID NO: 7)
DWLIFAADYSQIELRVLAHISKDENL

Motif C

Klenow Fragment
(SEQ ID NO: 8)
MIMQVHDELVFEVHKDDVD

Taq
(SEQ ID NO: 9)
MLLQVHDELVLEAPKERAE

Bst-f
(SEQ ID NO: 10)
LLLQVHDELILEAPKEEIE

Bsu-f
(SEQ ID NO: 11)
LLLQVHDELIFEAPKEEIE

The Bst-f numbering for the bolded and underlined motif A aspartate (D) residue is residue 381 in SEQ ID NO:1 (or residue 364 in SEQ ID NO:2; or residue 355 in SEQ ID NO:3). The motif C aspartate (D) and glutamate (E) residues are numbered 558 and 559 in SEQ ID NO:1 (or residues 541 and 542 in SEQ ID NO:2; or residues 532 and 533 in SEQ ID NO:3), respectively. While most DNA polymerases are known to include amino acids providing three carboxylate side chains in motifs A and C, some require only two carboxylate side chains during the catalysis. Residues 381 and 558 of SEQ ID NO:1 were picked for mutagenesis to investigate their effects on polymerase activity. These residues were substituted, using site-directed mutagenesis and an expression vector encoding the polymerase protein, with either glutamate (E) or asparagine (N). Again, the objective was to allow maintenance of the DNA and dNTP binding properties while inhibiting the polymerization chemistry step. A summary of key mutations is presented in Table 1.

TABLE 1

Summary of Key Mutations

| Mutant Name | Mutation | Position |
|---|---|---|
| CBT | Cys-optimized Bst enzyme with N-terminal modifications | N/A |

TABLE 1-continued

Summary of Key Mutations

| Mutant Name | Mutation | Position |
|---|---|---|
| TDE | D to E in Motif A | 381 of SEQ ID NO: 1 |
| | | 364 of SEQ ID NO: 2 |
| | | 355 of SEQ ID NO: 3 |
| BDE | D to E in Motif C | 558 of SEQ ID NO: 1 |
| | | 541 of SEQ ID NO: 2 |
| | | 532 of SEQ ID NO: 3 |
| TDN | D to N in Motif A | 381 of SEQ ID NO: 1 |
| | | 364 of SEQ ID NO: 2 |
| | | 355 of SEQ ID NO: 3 |

As described briefly below, the TDE and BDE mutant polymerases behaved substantially similarly. More specifically, both mutants were useful for binding and identifying cognate nucleotide during an examination reaction without incorporation. As well, neither mutant possessed catalytic incorporation activity in the presence of $Mg^{2+}$ ions. In contrast, the TDN mutant was inactive (i.e., being incapable of identifying cognate nucleotide in an examination step).

Crippled DNA Polymerase Reporters

Optionally, a crippled DNA polymerase is tagged with a luminescent tag, wherein closed-complex formation is monitored as a stable luminescence signal in the presence of the appropriate luminescence triggers (e.g., a radiation trigger or, in the case of chemiluminescent tags, chemical trigger). The unstable interaction of the crippled DNA polymerase with the template nucleic acid in the presence of an incorrect nucleotide results in a measurably weaker signal compared to the closed-complex formed in the presence of the next correct nucleotide. Additionally, a wash step prior to triggering luminescence could remove all polymerase molecules not bound in a stable closed-complex.

Optionally, a crippled DNA polymerase is tagged with an optical scattering tag, wherein closed-complex formation is monitored as a stable optical scattering signal. The unstable interaction of the crippled DNA polymerase with the nucleic acid in the presence of an incorrect nucleotide results in a measurably weaker signal compared to the closed-complex formed in the presence of the next correct nucleotide.

Optionally, the crippled DNA polymerase is tagged with a plasmonic nanoparticle tag, wherein the closed-complex formation is monitored as a shift in plasmonic resonance that is different from the plasmonic resonance in the absence of the closed-complex or the presence of a closed-complex including an incorrect nucleotide. The change in plasmon resonance may be due to the change in local dielectric environment in the closed-complex, or it may be due to the synchronous aggregation of the plasmonic nanoparticles on a cluster of clonally amplified nucleic acid molecules or another means that affects the plasmons differently in the closed-complex configuration.

Optionally, the crippled DNA polymerase is tagged with a Raman scattering tag, wherein the closed-complex formation is monitored as a stable Raman scattering signal. The unstable interaction of crippled DNA polymerase with the nucleic acid in the presence of an incorrect nucleotide results in a measurably weaker signal compared to the closed-complex formed in the presence of the next correct nucleotide.

Optionally, a next correct nucleotide is identified by a tag on a crippled DNA polymerase selected or modified to have a high affinity for nucleotides, wherein the polymerase binds to a nucleotide prior to binding to the template nucleic acid.

For example, the DNA polymerase X from the African Swine Fever virus has an altered order of substrate binding, where the polymerase first binds to a nucleotide, then binds to the template nucleic acid. Optionally, a polymerase is incubated with each type of nucleotide in separate compartments, where each compartment contains a different type of nucleotide and where the polymerase is labeled differently with a tag depending on the nucleotide with which it is incubated. In these conditions, unlabeled nucleotides are bound to differently labeled polymerases. The polymerases may be the same kind of polymerase bound to each nucleotide type or different polymerases bound to each nucleotide type. The differentially tagged polymerase-nucleotide complexes may be added simultaneously to any step of the sequencing reaction. Each polymerase-nucleotide complex binds to a template nucleic acid whose next base is complementary to the nucleotide in the polymerase-nucleotide complex. The next correct nucleotide is identified by the tag on the polymerase carrying the nucleotide. The interrogation of the next template base by the labeled polymerase-nucleotide complex may be performed under non-incorporating and/or examination conditions, where once the identity of the next template base is determined, the complex is destabilized and removed, sequestered, and/or diluted and a separate incorporation step is performed in a manner ensuring that only one nucleotide is incorporated.

A common method of introducing a detectable tag on a polymerase optionally involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-hydroxysuccinimide (NHS) chemistry is employed at pH ranges where only the N-terminal amines are reactive (for instance, pH 7), such that only a single tag is added per polymerase.

Optionally, the tag attached to the crippled DNA polymerase is a charge tag, such that the formation of stable closed-complex can be detected by electrical means by measuring changes in local charge density around the template nucleic acids. Methods for detecting electrical charges are well known in the art, including methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a crippled DNA polymerase including a peptide tag has a total isoelectric point below about 5 or above about 9. A charge tag may be any moiety which is positively or negatively charged. The charge tag may include additional moieties including mass and/or labels such as dyes. Optionally, the charge tag possesses a positive or negative charge only under certain reaction conditions such as changes in pH.

A crippled DNA polymerase may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl]coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies; Carlsbad Calif.) and Fluorophores Guide (Promega; Madison, WI), which are incorporated herein by reference in their entireties. Exemplary quenches include, but are not limited to, ZEN, IBFQ, BHQ-1, BHQ-2, DDQ-I, DDQ-11, Dabcyl, Qxl quencher, Iowa Black RQ, and IRDye QC-1.

Optionally, a conformationally sensitive dye may be attached close to the active site of the crippled DNA polymerase without affecting the polymerization ability or fidelity of the polymerase; wherein a change in conformation, or a change in polar environment due to the formation of a closed-complex is reflected as a change in fluorescence or absorbance properties of the dye. Common fluorophores such as Cy3 and fluorescein are known to have strong solvatochromatic response to polymerase binding and closed-complex formation, to the extent that the formation of closed-complex can be distinguished clearly from the binary polymerase-nucleic acid complex. Optionally, the closed-complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene]cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided by Tsai et al., in "Site-Specific Labeling of T7 DNA Polymerase with a Conformationally Sensitive Fluorophore and Its Use in Detecting Single-Nucleotide Polymorphisms," *Analytical Biochemistry* 384: 136-144 (2009), which is incorporated by reference herein in its entirety.

Optionally, a polymerase is tagged with a fluorophore at a position that could sense closed-complex formation without interfering with the reaction. The polymerase may be a native or modified polymerase. Modified polymerases include those with one or more amino acid chemical modifications, mutations, additions, and/or deletions. Optionally, one or more, but not all, cysteine amino acids are mutated to another amino acid, such as alanine. In this case, the remaining one or more cysteines are used for site-specific conjugation to a fluorophore. Alternatively, one or more amino acids are mutated to a reactive amino acid suitable for fluorophore conjugation, such as cysteines or amino acids including primary amines.

Optionally, binding between a crippled DNA polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the crippled DNA polymerase/nucleic-acid interaction may be monitored by scattering signal originating from the polymerase or tags attached to the polymerase, for instance, nanoparticle tags.

Conditions for Forming and Manipulating Closed-Complexes

As used herein, a closed-complex can be a ternary complex that includes a crippled DNA polymerase, primed template nucleic acid, and nucleotide. The closed-complex may be in a pre-chemistry conformation, wherein a nucleotide is sequestered but not incorporated. The closed-complex may alternatively be in a pre-translocation conformation, wherein a nucleotide is incorporated by formation of a phosphodiester bond with the 3'-end of the primer in the primed template nucleic acid. The closed-complex may be formed in the absence of catalytic metal ions or deficient levels of catalytic metal ions, thereby physically sequestering the next correct nucleotide within the polymerase active site without chemical incorporation. Optionally, the sequestered nucleotide may be a non-incorporable nucleotide. The closed-complex may be formed in the presence of catalytic metal ions, where the closed-complex includes a nucleotide analog which is incorporated, but a PPi is not capable of release. In this instance, the closed-complex is stabilized in a pre-translocation conformation. Optionally, a pre-translocation conformation is stabilized by chemically cross-linking the polymerase. Optionally, the closed-complex may be stabilized by external means. In some instances, the closed-complex may be stabilized by allosteric binding of small molecules, or macromolecules such as antibodies or aptamers. Optionally, closed-complex may be stabilized by pyrophosphate analogs that bind close to the active site with high affinity, preventing translocation of the polymerase.

As used herein, a stabilized closed-complex or stabilized ternary complex refers to a polymerase trapped at the polymerization initiation site (3'-end of the primer) of the primed template nucleic acid by one or a combinations of means, including but not limited to, crosslinking the thumb and finger domains in the closed conformation, binding of an allosteric inhibitor that prevents return of the polymerase to an open conformation, binding of pyrophosphate analogs that trap polymerase in the pre-translocation step, absence of catalytic metal ions in the active site of the polymerase, and addition of a metal ions such as nickel, tin and $Sr^{2+}$ as substitutes for a catalytic metal ion. As such, the polymerase may be trapped at the polymerization initiation site even after the incorporation of a nucleotide. Therefore, the polymerase may be trapped in the pre-chemistry conformation, pre-translocation step, post-translocation step or any intermediate step thereof. Thus, allowing for sufficient examination and identification of the next correct nucleotide or base.

As described herein, a polymerase-based, sequencing-by-binding reaction generally involves providing a primed template nucleic acid with a polymerase and one or more types of nucleotides, wherein the nucleotides may or may not be complementary to the next base of the primed template nucleic acid, and examining the interaction of the polymerase with the primed template nucleic acid under conditions wherein either chemical incorporation of a nucleotide into the primed template nucleic acid is disabled or severely inhibited in the pre-chemistry conformation or one or more complementary nucleotide incorporation occurs at the 3'-end of the primer. Optionally, wherein the pre-chemistry conformation is stabilized prior to nucleotide incorporation, preferably using stabilizers, a separate incorporation step may follow the examination step to incorporate a single nucleotide to the 3'-end of the primer. Optionally, where a single nucleotide incorporation occurs, the pre-translocation conformation may be stabilized to facilitate examination and/or prevent subsequent nucleotide incorporation.

As indicated above, the presently described methods for sequencing a nucleic acid include an examination step. The examination step involves binding a polymerase to the polymerization initiation site of a primed template nucleic acid in a reaction mixture including one or more nucleotides, and monitoring the interaction. Optionally, a nucleotide is sequestered within the polymerase-primed template nucleic acid complex to form a closed-complex, under conditions in which incorporation of the enclosed nucleotide by the polymerase is attenuated or inhibited. Optionally a stabilizer is added to stabilize the ternary complex in the presence of the next correct nucleotide. This closed-complex is in a stabilized or polymerase-trapped pre-chemistry conformation. A closed-complex allows for the incorporation of the enclosed nucleotide but does not allow for the incorporation of a subsequent nucleotide. This closed-complex is in a stabilized or trapped pre-translocation conformation. Optionally, the polymerase is trapped at the polymerization site in its closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped closed-complex provides information about the identity of the next base on the nucleic acid template.

Optionally, a closed-complex is released from its trapped or stabilized conformation, which may allow for nucleotide incorporation to the 3'-end of the template nucleic acid primer. The closed-complex can be destabilized and/or released by modulating the composition of the reaction conditions. In addition, the closed-complex can be destabilized by electrical, magnetic, and/or mechanical means. Mechanical means include mechanical agitation, for example, by using ultrasound agitation. Mechanical vibration destabilizes the closed-complex and suppresses binding of the polymerase to the DNA. Thus, rather than a wash step where the examination reaction mixture is replaced with an incorporation mixture, mechanical agitation may be used to remove the polymerase from the template nucleic acid, enabling cycling through successive incorporation steps with a single nucleotide addition per step.

Any combination of closed-complex stabilization or closed-complex release reaction conditions and/or methods may be combined. For example, a polymerase inhibitor that stabilizes a closed-complex may be present in the examination reaction with a catalytic ion, which functions to release the closed-complex. In the aforementioned example, the closed-complex may be stabilized or released, depending on the polymerase inhibitor properties and concentration, the concentration of the catalytic metal ion, other reagents and/or conditions of the reaction mixture, and any combination thereof.

The closed-complex can be stabilized under reaction conditions where covalent attachment of a nucleotide to the 3'-end of the primer in the primed template nucleic acid is attenuated. Optionally, the closed-complex is in a pre-chemistry conformation or ternary complex. Optionally, the closed-complex is in a pre-translocation conformation. The formation of this closed-complex can be initiated and/or stabilized by modulating the availability of a catalytic metal ion that permits closed-complex release and/or chemical incorporation of a nucleotide to the primer in the reaction mixture. Exemplary metal ions include, but are not limited to, magnesium, manganese, cobalt, and barium. Catalytic ions may be any formulation, for example, salts such as $MgCl_2$, $Mg(CH_3CO_2)_2$, and $MnCl_2$.

The selection and/or concentration of the catalytic metal ion may be based on the polymerase and/or nucleotides in the sequencing reaction. For example, the HIV reverse transcriptase utilizes magnesium for nucleotide incorporation (N Kaushik, *Biochemistry* 35:11536-11546 (1996), and H P Patel, *Biochemistry* 34:5351-5363 (1995), which are incorporated by reference herein in their entireties). The rate of closed-complex formation using magnesium versus manganese can be different depending on the polymerase and the identity of the nucleotide. Thus, the stability of the closed-complex may differ depending on catalytic metal ion, polymerase, and/or nucleotide identity. Further, the concentration of catalytic ion necessary for closed-complex stabilization may vary depending on the catalytic metal ion, polymerase, and/or nucleotide identity and can be readily determined using the guidance provided herein. For example, nucleotide incorporation may occur at high catalytic ion concentrations of one metal ion but does not occur at low concentrations of the same metal ion, or vice versa. Therefore, modifying metal ion identity, metal ion concentration, polymerase identity, and/or nucleotide identity allows for controlled examination reaction conditions.

The closed-complex may be formed and/or stabilized by sequestering, removing, reducing, omitting, and/or chelating a catalytic metal ion during the examination step of the sequencing reaction so that closed-complex release and/or chemical incorporation does not occur. Chelation includes any procedure that renders the catalytic metal ion unavailable for nucleotide incorporation, including using EDTA and/or EGTA. A reduction includes diluting the concentration of a catalytic metal ion in the reaction mixture. The reaction mixture can be diluted or replaced with a solution including a non-catalytic ion, which permits closed-complex formation, but inhibits nucleotide incorporation. Non-catalytic ions include, but are not limited to, calcium, strontium, scandium, titanium, vanadium, chromium, iron, cobalt, nickel, copper, zinc, gallium, germanium, arsenic, selenium, rhodium, and strontium. Optionally, $Ni^{2+}$ is provided in an examination reaction to facilitate closed-complex formation. Optionally, $Sr^{2+}$ is provided in an examination reaction to facilitate closed-complex formation. Optionally, a non-catalytic metal ion that inhibits polymerase-mediated incorporation and a catalytic metal ion are both present in the reaction mixture, wherein one ion is present in a higher effective concentration than the other. In the provided methods, a non-catalytic ion such as cobalt can become catalytic (i.e., facilitate nucleotide incorporation) at high concentrations. Thus, optionally, a low concentration of a non-catalytic metal ion that inhibits polymerase-mediated incorporation is used to facilitate ternary complex formation, and a higher concentration of the non-catalytic metal ion is used to facilitate incorporation.

Non-catalytic ions may be added to a reaction mixture under examination conditions. The reaction may already include nucleotides. Optionally, non-catalytic ions are complexed to one or more nucleotides and complexed nucleotides are added to the reaction mixture. Non-catalytic ions can complex to nucleotides by mixing nucleotides with non-catalytic ions at elevated temperatures (about 80° C.). For example, a chromium nucleotide complex may be added to a mixture to facilitate closed-complex formation and stabilization. Optionally, a chromium nucleotide complex is a chromium monodentate, bidentate, or tridentate complex. Optionally, a chromium nucleotide complex is an α-monodentate, or β-γ-bidentate nucleotide.

Optionally, a closed-complex is formed between a crippled DNA polymerase, primed template nucleic acid, and nucleotide in reaction conditions including $Sr^{2+}$ wherein $Sr^{2+}$ promotes the formation of the closed-complex. The presence of $Sr^{2+}$ can allow for the favorable formation of a closed-complex including a next correct nucleotide over the formation a complex including an incorrect nucleotide. The $Sr^{2+}$ ion may be present at concentrations from about 0.01 mM to about 30 mM. Optionally, $Sr^{2+}$ is present as 10 mM $SrCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the crippled DNA polymerase and primed template nucleic acid. Optionally, the binding interaction may be performed under conditions that stabilize the ternary interactions between the polymerase, the primed template nucleic acid, and the next correct nucleotide. After examination, a wash step removes unbound nucleotides, and $Mg^{2+}$ is added to the reaction to induce pyrophosphate (PPi) cleavage and nucleotide incorporation. Optionally, the wash step includes $Sr^{2+}$ to maintain the stability of the ternary complex, preventing the dissociation of the ternary complex. The reaction may be repeated until a desired sequence read-length is obtained.

Optionally, a closed-complex is formed between a crippled DNA polymerase, primed template nucleic acid, and nucleotide in reaction conditions including $Ni^{2+}$, wherein $Ni^{2+}$ promotes the formation of the closed-complex. The presence of $Ni^{2+}$ can allow for the favorable formation of a closed-complex including a next correct nucleotide over the formation a complex including an incorrect nucleotide. The $Ni^{2+}$ ion may be present at concentrations from about 0.01 mM to about 30 mM. Optionally, $Ni^{2-}$ is present as 10 mM $NiCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Mg^{2+}$ is added to the reaction to induce pyrophosphate (PPi) cleavage and nucleotide incorporation. Optionally, the wash buffer includes $Ni^{2+}$ to maintain the stability of the ternary complex, preventing the dissociation of the ternary complex. The reaction may be repeated until a desired sequence read length is obtained.

Optionally, a closed-complex is formed between a crippled DNA polymerase, primed template nucleic acid, and nucleotide in reaction conditions including non-catalytic concentrations of $Co^{2+}$, wherein $Co^{2+}$ promotes the formation of the closed-complex. The presence of non-catalytic concentrations of $Co^{2+}$ can allow for the favorable formation of a closed-complex including a next correct nucleotide over the formation a complex including an incorrect nucleotide. The $Co^{2+}$ ion may be present at concentrations from about 0.01 mM to about 0.5 mM. Optionally, $Co^{2+}$ is present as 0.5 mM $CoCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each of the dNTPs (e.g., dATP, dTTP, dCTP, dGTP) in the presence of $Co^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Co^{2+}$ at a catalytic concentration is added to the reaction to induce pyrophosphate (PPi) cleavage and nucleotide incorporation. Optionally, the wash buffer includes non-catalytic amounts of $Co^{2+}$ to maintain the stability of the ternary complex, preventing the dissociation of the ternary complex. The reaction may be repeated until a desired sequence read length is obtained.

Optionally, a catalytic metal ion may facilitate the formation of a closed-complex without subsequent nucleotide incorporation and closed-complex release. Optionally, a concentration of 0.5, 1, 2, 3, 4, 5, 6, 7, 8, 9, or 10 μM $Mg^{2+}$ in a reaction mixture can induce conformational change of a polymerase to form a closed-complex without subsequent nucleotide incorporation, PPi and closed-complex release. Optionally, the concentration of $Mg^{2+}$ is from about 0.5 μM to about 10 μM, from about 0.5 μM to about 5 μM, from about 0.5 μM to about 4 μM, from about 0.5 μM to about 3 μM, from about μM to about 5 μM, from about 1 μM to about 4 μM, and from about 1 μM to about 3 μM.

Optionally, the concentration of available catalytic metal ion in the sequencing reaction which is necessary to allow nucleotide incorporation is from about 0.001 mM to about 10 mM, from about 0.01 mM to about 5 mM, from about 0.01 mM to about 3 mM, from about 0.01 mM to about 2 mM, from about 0.01 mM to about 1 mM, from about 0.05 mM to about 10 mM, from about 0.05 mM to about 5 mM, from about 0.05 mM to about 3 mM, from about 0.05 to about 2 mM, or from about 0.05 mM to about 1 mM. Optionally, the concentration of catalytic metal ion is from 5 mM to 50 mM. Optionally, the concentration of catalytic metal ion is from 5 mM to 15 mM, or about 10 mM.

A non-catalytic ion may be added to the reaction mixture at any stage including before, during, or after any of the following reaction steps: providing a primed template nucleic acid, providing a polymerase, formation of a binary complex, providing a nucleotide, formation of a pre-chemistry closed-complex, nucleotide incorporation, formation of a pre-translocation closed-complex, and formation of a post-translocation conformation. The non-catalytic ion may be added to the reaction mixture during wash steps. The non-catalytic ion may be present through the reaction in the reaction mixture. For example, a catalytic ion is added to the reaction mixture at concentrations which dilute the non-catalytic metal ion that inhibits polymerase-mediated incorporation, allowing for nucleotide incorporation.

The ability of catalytic and non-catalytic ions to modulate nucleotide incorporation may depend on conditions in the reaction mixture including, but not limited to, pH, ionic strength, chelating agents, chemical cross-linking, modified polymerases, non-incorporable nucleotides, mechanical or vibration energy, and electric fields.

Optionally, the concentration of non-catalytic metal ion that inhibits polymerase-mediated incorporation in the sequencing reaction necessary to allow for closed-complex formation without nucleotide incorporation is from about 0.1 mM to about 50 mM, from about 0.1 mM to about 40 mM, from about 0.1 mM to about 30 mM, from about 0.1 mM to about 20 mM, from about 0.1 mM to about 10 mM, from about 0.1 mM to about 5 mM, from about 0.1 to about 1 mM, from about 1 mM to about 50 mM, from about 1 to about 40 mM, from about 1 mM to about 30 mM, from about 1 mM to about 20 mM, from about 1 mM to about 10 mM, from about 1 mM to about 5 mM, from about 2 mM to about 30 mM, from about 2 mM to about 20 mM, from about 2 mM to about 10 mM, or any concentration within these ranges.

A closed-complex may be formed and/or stabilized by the addition of a polymerase inhibitor to the examination reaction mixture. Inhibitor molecules phosphonoacetate (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its closed-complex conformation before or after the incorporation of a nucleotide, and forcing the polymerase to be bound to the template nucleic acid until the inhibitor molecules are not available in the reaction mixture by removal, dilution or chelation.

Thus, provided is a method for sequencing a template nucleic acid molecule including an examination step including providing a template nucleic acid molecule primed with a primer; contacting the primed template nucleic acid molecule with a first reaction mixture including a polymerase, a polymerase inhibitor and at least one unlabeled nucleotide molecule; monitoring the interaction of the polymerase with the primed template nucleic acid molecule in the presence of the unlabeled nucleotide molecule without incorporation of the nucleotide into the primer of the primed template nucleic acid molecule; and identifying the nucleotide that is complementary to the next base of the primed template nucleic acid molecule by the monitored interaction. The polymerase inhibitor prevents the incorporation of the unlabeled nucleotide molecule into the primer of the primer template nucleic acid. Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Detection Platforms: Instrumentation for Detecting the Closed-Complex

The interaction between the crippled DNA polymerase and the template nucleic acid in the presence of nucleotides can be monitored without the use of an exogenous label. For example, the sequencing reaction may be monitored by detecting the change in refractive index, fluorescence emission, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label-free detection schemes that detect the added mass or refractive index due to polymerase binding in a closed-complex with a template nucleic acid.

Optionally, detecting a change in refractive index is accomplished by one or a combination of means, including, but not limited to, surface plasmon resonance sensing, localized plasmon resonance sensing, plasmon-photon coupling sensing, transmission sensing through sub-wavelength nanoholes (enhanced optical transmission), photonic crystal sensing, interferometry sensing, refraction sensing, guided mode resonance sensing, ring resonator sensing, or ellipsometry sensing. Optionally, nucleic acid molecules may be localized to a surface, wherein the interaction of polymerase with nucleic acids in the presence of various nucleotides may be measured as a change in the local refractive index.

Optionally, the template nucleic acid is tethered to or localized appropriately on or near a surface, such that the interaction of polymerase and template nucleic acid in the presence of nucleotides changes the light transmitted across or reflected from the surface. The surface may contain nanostructures. Optionally, the surface is capable of sustaining plasmons or plasmon resonance. Optionally, the surface is a photonic substrate, not limited to a resonant cavity, resonant ring or photonic crystal slab. Optionally, the surface is a guided mode resonance sensor. Optionally, the nucleic acid is tethered to, or localized appropriately on or near a nanohole array, a nanoparticle or a microparticle, such that the interaction of polymerase and template nucleic acid in the presence of nucleotides changes the absorbance, scattering, reflection or resonance of the light interacting with the microparticle or nanoparticle.

Optionally, a nanohole array on a gold surface is used as a refractive index sensor. The template nucleic acid may be attached to a metal surface by standard thiol chemistry, incorporating the thiol group on one of the primers used in a PCR reaction to amplify the DNA. When the dimensions of the nanohole array are appropriately tuned to the incident light, binding of the polymerase to the template nucleic acid in the presence of nucleotides can be monitored as a change in light transmitted across the nanoholes. For both the labeled and label-free schemes, simple and straightforward measurement of equilibrium signal intensity may reveal the formation of a stable closed-complex.

Optionally, nucleic acid molecules are localized to a surface capable of sustaining surface plasmons, wherein the change in refractive index caused by the polymerase interaction with localized nucleic acids may be monitored through the change in the properties of the surface plasmons, wherein further, said properties of surface plasmons may include surface plasmon resonance. Surface plasmons, localized surface plasmons (LSP), or surface plasmon polaritons (SPP), arise from the coupling of electromagnetic waves to plasma oscillations of surface charges. LSPs are confined to nanoparticle surfaces, while SPPs and are confined to high electron density surfaces, at the interface between high electron mobility surfaces and dielectric media. Surface plasmons may propagate along the direction of the interface, whereas they penetrate into the dielectric medium only in an evanescent fashion. Surface plasmon resonance conditions are established when the frequency of incident electromagnetic radiation matches the natural frequency of oscillation of the surface electrons. Changes in dielectric properties at the interface, for instance due to binding or molecular crowding, affects the oscillation of surface electrons, thereby altering the surface plasmon resonance wavelength. Surfaces capable of surface plasmon resonance include, in a non-limiting manner, nanoparticles, clusters and aggregates of nanoparticles, continuous planar surfaces, nanostructured surfaces, and microstructured surfaces. Materials such as gold, silver, aluminum, high conductivity metal oxides (e.g., indium tin oxide, zinc oxide, tungsten oxide) are capable of supporting surface plasmon resonance at their surfaces.

Optionally, a single nucleic acid molecule, or multiple clonal copies of a nucleic acid, are attached to a nanoparticle, such that binding of polymerase to the nucleic acid causes a shift in the localized surface plasmon resonance (LSPR). Light incident on the nanoparticles induces the conduction electrons in them to oscillate collectively with a resonant frequency that depends on the nanoparticles' size, shape and composition. Nanoparticles of interest may assume different shapes, including spherical nanoparticles, nanorods, nanopyramids, nanodiamonds, and nanodiscs. As a result of these LSPR modes, the nanoparticles absorb and scatter light so intensely that single nanoparticles are easily observed by eye using dark-field (optical scattering) microscopy. For example, a single 80-nm silver nanosphere scatters 445-nm blue light with a scattering cross-section of $3\times10^{-2}$ m$^2$, a million-fold greater than the fluorescence cross-section of a fluorescein molecule, and a thousand fold greater than the cross-section of a similarly sized nanosphere filled with fluorescein to the self-quenching limit. Optionally, the nanoparticles are plasmon-resonant particles configured as ultra-bright, nanosized optical scatters with a scattering peak anywhere in the visible spectrum. Plasmon-resonant particles are advantageous as they do not bleach. Optionally, plasmon-resonant particles are prepared, coated with template nucleic acids, and provided in a reaction mixture including a polymerase and one or more nucleotides, wherein a polymerase-template nucleic acid-particle interaction is detected. One or more of the aforementioned steps may be based on or derived from one or more methods disclosed by Schultz et al., in *PNAS* 97:996-1001 (2000), which is incorporated by reference herein in its entirety.

The very large extinction coefficients at resonant wavelength enables noble-metal nanoparticles to serve as extremely intense labels for near-surface interactions. Optionally, polymerase interaction with nanoparticle-localized DNA results in a shift in the resonant wavelength. The change in resonant wavelength due to binding or binding interactions can be measured in one of many ways. Optionally, the illumination is scanned through a range of wavelengths to identify the wavelength at which maximum scattering is observed at an imaging device. Optionally, broadband illumination is utilized in conjunction with a dispersive element near the imaging device, such that the resonant peak is identified spectroscopically. Optionally, the nanoparticle system may be illuminated at its resonant wavelength, or near its resonant wavelength, and any binding interactions may be observed as a drop in intensity of light scattered as the new resonant wavelength shifts away from the illumination wavelength. Depending on the positioning of the illuminating wavelength, interactions may even appear as an increase in nanoparticle scattering as the resonance peak shifts towards the illumination wavelength. Optionally, DNA-attached-nanoparticles may be localized to a surface, or, alternatively, the DNA-attached-nanoparticles may be suspended in solution. A comprehensive review of biosensing using nanoparticles is described by Anker et al., in *Nature Materials* 7: 442-453 (2008), which is incorporated in its entirety herein by reference.

Optionally, nano-features capable of LSPR are lithographically patterned on a planar substrate. The two dimensional patterning of nano-features has advantages in multiplexing and high-throughput analysis of a large number of different nucleic acid molecules. Optionally, gold nanoposts are substrates for surface plasmon resonance imaging detection of polymerase-template nucleic acid interactions, wherein the nucleic acids are attached to the nanoposts. Nanostructure size and period can influence surface plasmon resonance signal enhancement, optionally, providing a 2, 3, 4, 5, 6, 7, 8-fold or higher signal amplification when compared to control films.

Optionally, surface plasmon resonance may be sustained in planar surfaces. A number of commercial instruments based on the Kretschmann configuration (e.g., Biacore, Uppsala, Sweden) and surface plasmon resonance imaging (e.g., GWC Technologies; Madison, WI; or Horiba; Kyoto, Japan) are available and have well established protocols for attaching DNA to their surfaces, as single spots and in multiplexed array patterns. In the Kretschmann configuration, a metal film, typically gold, is evaporated onto the side of a prism and incident radiation is launched at an angle to excite the surface plasmons. An evanescent wave penetrates through the metal film exciting plasmons on the other side, where it may be used to monitor near-surface and surface interactions near the gold film. At the resonant angle, the light reflected from the prism-gold interface is severely attenuated. Assuming fixed wavelength illumination, binding interactions may be examined by monitoring both the intensity of the reflected light at a fixed angle close to the resonant angle, as well as by monitoring the changes in angle of incidence required to establish surface plasmon resonance conditions (minimum reflectivity). When a 2D imaging device such as a CCD or CMOS camera is utilized to monitor the reflected light, the entire illumination area may be imaged with high resolution. This method is called surface plasmon resonance imaging (SPRi). It allows high throughput analysis of independent regions on the surface simultaneously. Broadband illumination may also be used, in a fixed angle configuration, wherein the wavelength that is coupled to the surface plasmon resonance is identified spectroscopically by looking for dips in the reflected spectrum. Surface interactions are monitored through shifts in the resonant wavelength.

Surface plasmon resonance is a well-established method for monitoring protein-nucleic acid interactions, and there exist many standard protocols both for nucleic acid attachment as well as for analyzing the data. Illustrative references from the literature include Cho et al., "Binding Kinetics of DNA-Protein Interaction Using Surface Plasmon Resonance," *Protocol Exchange*, May 22, 2013; and Brockman et al., "A Multistep Chemical Modification Procedure To Create DNA Arrays on Gold Surfaces for the Study of Protein-DNA Interactions with Surface Plasmon Resonance Imaging," *Journal of the American Chemical Society* 121: 8044-51 (1999), both of which are incorporated by reference herein in their entireties.

Polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, extraordinary optical transmission (EOT) through a nanoholes array may be used to monitor nucleic-acid/polymerase interactions. Light transmitted across subwavelength nanoholes in plasmonic metal films is higher than expected from classical electromagnetic theory. This enhanced optical transmission may be explained by considering plasmonic resonant coupling to the incident radiation, whereby at resonant wavelength, a larger than anticipated fraction of light is transmitted across the metallic nanoholes. The enhanced optical transmission is dependent on the dimensions and pitch of the nanoholes, properties of the metal, as well as the dielectric properties of the medium on either side of the metal film bearing the nanoholes. In the context of a biosensor, the transmissivity of the metallic nanohole array depends on the refractive index of the medium contacting the metal film, whereby, for instance, the interaction of polymerase with nucleic acid attached to the metal surface may be monitored as a change in intensity of light transmitted across the nanoholes array. Instrumentation and alignment requirements when using the EOT/plasmonic nanohole array approach of surface plasmon resonance may be employed using very compact optics and imaging elements. Low power LED illumination and a CMOS or CCD camera may suffice to implement robust EOT plasmonic sensors. An exemplary nanohole array-based surface plasmon resonance sensing device is described by Escobedo et al., in "Integrated Nanohole Array Surface Plasmon Resonance Sensing Device Using a Dual-Wavelength Source," *Journal of Micromechanics and Microengineering* 21: 115001 (2011), which is herein incorporated by reference in its entirety.

The plasmonic nanohole array may be patterned on an optically opaque layer of gold (greater than 50 nm thickness) deposited on a glass surface. Optionally, the plasmonic nanohole array may be patterned on an optically thick film of aluminum or silver deposited on glass. Optionally, the nanohole array is patterned on an optically thick metal layer deposited on low refractive index plastic. Patterning plasmonic nanohole arrays on low refractive index plastics enhances the sensitivity of the device to refractive index changes by better matching the refractive indices on the two sides of the metal layer. Optionally, refractive index sensitivity of the nanohole array is increased by increasing the distance between holes. Optionally, nanohole arrays are fabricated by replication, for example, by embossing, casting, imprint-lithography, or template-stripping. Optionally, nanohole arrays are fabricated by self-assembly using colloids. Optionally, nanohole arrays are fabricated by projection direct patterning, such as laser interference lithography.

A nano-bucket configuration may be preferable to a nanohole configuration. In the nanohole configuration, the bottom of the nano-feature is glass or plastic or other appropriate dielectric, whereas in the nano-bucket configuration, the bottom of the nano-feature includes a plasmonic metal. The nano-bucket array advantageously is relatively simple to fabricate while maintaining the transmission sensitivity to local refractive index.

Optionally, the nanohole array plasmonic sensing is combined with lens-free holographic imaging for large area imaging in an inexpensive manner. Optionally, a plasmonic biosensing platform includes a plasmonic chip with nanohole arrays, a light-emitting diode source configured to illuminate the chip, and a CMOS imager chip to record diffraction patterns of the nanoholes, which is modulated by molecular binding events on the surface. The binding events may be the formation of a closed-complex between a polymerase and a template nucleic acid in the presence of a nucleotide.

The methods to functionalize surfaces (for nucleic acid attachment) for surface plasmon resonance sensing may be directly applied to EOT nanohole arrays as both sensing schemes employ similar metal surfaces to which nucleic acids need to be attached.

Optionally, the refractive index changes associated with polymerase/nucleic acid interaction may be monitored on nanostructured surfaces that do not support plasmons. Optionally, guided mode resonance may be used to monitor the polymerase/nucleic-acid interaction. Guided-mode resonance or waveguide-mode resonance is a phenomenon wherein the guided modes of an optical waveguide can be excited and simultaneously extracted by the introduction of a phase-matching element, such as a diffraction grating or prism. Such guided modes are also called "leaky modes," as they do not remain guided and have been observed in one and two-dimensional photonic crystal slabs. Guided mode resonance may be considered a coupling of a diffracted mode to a waveguide mode of two optical structured placed adjacent or on top of each other. For instance, for a diffraction grating placed on top of an optical waveguide, one of the diffracted modes may couple exactly into the guided mode of the optical waveguide, resulting in propagation of that mode along the waveguide. For off-resonance conditions, no light is coupled into the waveguide, so the structure may appear completely transparent (if dielectric waveguides are used). At resonance, the resonant wavelength is strongly coupled into the waveguide and may be couple out of the structure depending on downstream elements from the grating-waveguide interface. In cases where the grating coupler is extended over the entire surface of the waveguide, the light cannot be guided, as any light coupled in is coupled out at the next grating element. Therefore, in a grating waveguide structure, resonance is observed as a strong reflection peak, whereas the structure is transparent to off-resonance conditions. The resonance conditions are dependent on angle, grating properties, polarization and wavelength of incident light. For cases where the guided mode propagation is not present, for instance due to a grating couple to the entire surface of the waveguide, the resonant mode may also be called leaky-mode resonance, in light of the strong optical confinement and evanescent propagation of radiation in a transverse direction from the waveguide layer. Change in dielectric properties near the grating, for instance due to binding of biomolecules affects the coupling into the waveguide, thereby altering the resonant conditions. Optionally, where nucleic acid molecules are attached to the surface of grating waveguide structures, the polymerase/nucleic-acid interaction may be monitored as a change in wavelength of the leaky mode resonance.

A diffraction element may be used directly on a transparent substrate without an explicit need for a waveguide element. The change in resonance conditions due to interactions near the grating nanostructure may be monitored as resonant wavelength shifts in the reflected or transmitted radiation.

Reflected light from a nucleic acid attached guided mode resonant sensor may be used to monitor the polymerase/nucleic-acid interaction. A broadband illumination source may be employed for illumination, and a spectroscopic examination of reflected light could reveal changes in local refractive index due to polymerase binding.

Optionally, a broadband illumination may be used and the transmitted light may be examined to identify resonant shifts due to polymerase interaction. A linearly polarized narrow band illumination may be used, and the transmitted light may be filtered through a cross-polarizer; wherein the transmitted light is completely attenuated due to the crossed polarizers excepting for the leaky mode response whose polarization is modified. This implementation converts refractive index monitoring to a simple transmission assay that may be monitored on inexpensive imaging systems. Published material describe the assembly of the optical components. See, Nazirizadeh et al., "Low-Cost Label-Free Biosensors Using Photonic Crystals Embedded between Crossed Polarizers," *Optics Express* 18: 19120-19128 (2010), which is incorporated herein by reference in its entirety.

In addition to nanostructured surfaces, plain, unstructured surfaces may also be used advantageously for monitoring refractive index modulations. Optionally, interferometry may be employed to monitor the interaction of polymerase with nucleic acid bound to an un-structured, optically transparent substrate. Nucleic acid molecules may be attached to the top surface of a glass slide by any means known in the art, and the system illuminated from the bottom surface of the glass slide. There are two reflection surfaces in this configuration, one reflection from the bottom surface of the glass slide, and the other from the top surface which has nucleic acid molecules attached to it. The two reflected waves may interfere with each other causing constructive or destructive interference based on the path length differences, with the wave reflected from the top surface modulated by the changes in dielectric constant due to the bound nucleic acid molecules (and subsequently by the interaction of polymerase with the bound nucleic acid molecules). With the reflection from the bottom surface unchanged, any binding to the nucleic acid molecules may be reflected in the phase difference between the beams reflected from the top and bottom surfaces, which in turn affects the interference pattern that is observed. Optionally, bio-layer interferometry is used to monitor the nucleic acid/polymerase interaction. Bio-layer interferometry may be performed on commercial devices such as those sold by Pall Forte Bio corporation (Menlo Park, CA).

Optionally, the reflected light from the top surface is selectively chosen by using focusing optics. The reflected light from the bottom surface is disregarded because it is not in the focal plane. Focusing only on the nucleic-acid-attached top surface, the light collected by the focusing lens includes a planar wave, corresponding to the partially reflected incident radiation, and a scattered wave, corresponding to the radiations scattered in the collection direction by molecules in the focal plane. These two components may be made to interfere if the incident radiation is coherent. This scattering based interferometric detection is extremely sensitive and can be used to detect down to single protein molecules.

Optionally, a field-effect transistor (FET) is configured as a biosensor for the detection of a closed-complex. A gate terminal of the FET is modified by the addition of template nucleic acids. The binding of a polymerase including a charged tag results in changes in electrochemical signals. Binding of a polymerase with a next correct nucleotide to the template nucleic acid provides different signals than polymerase binding to a template nucleic acid in the presence of other incorrect nucleotides, where each incorrect nucleotide may also provide a different signal. Optionally, polymerase interactions with a template nucleic acid are monitored using FET without the use of a an exogenous label on the polymerase, primed template nucleic acid, or nucleotide. Optionally, the pH change that occurs due to release of $H^+$ ions during the incorporation reaction is detected using a FET. Optionally, the polymerase includes a tag that generates continuous $H^+$ ions that is detected by the FET. Optionally, the continuous $H^+$ ion generating tag is an ATP synthase. Optionally, the continuous $H^+$ ion generation tag is palladium, copper or another catalyst. Optionally, the release of a PPi after nucleotide incorporation is detected using FET. For example, one type of nucleotide may be provided to a reaction at a time. Once the next correct nucleotide is added and conditions allow for incorporation, PPi is cleaved, released, and detected using FET, therefore identifying the next correct nucleotide and the next base. Optionally, template nucleic acids are bound to walls of a nanotube. Optionally, a polymerase is bound to a wall of a nanotube. FET is advantageous for use as a sequencing sensor due to its small size and low weight, making it appropriate for use as a portable sequencing monitoring component. Details of FET detection of molecular interactions are described by Kim et al., in "An FET-Type Charge Sensor for Highly Sensitive Detection of DNA Sequence," *Biosensors and Bioelectronics, Microsensors and Microsystems* 20: 69-74 (2004), doi:10.1016/j.bios.2004.01.025; and by Star et al., in "Electronic Detection of Specific Protein Binding Using Nanotube FET Devices," *Nano Letters* 3: 459-63 (2003), doi:10.1021/nl0340172, which are incorporated by reference herein in their entireties.

Optionally, the crippled DNA polymerase includes a fluorescent tag. To monitor polymerase-nucleic acid interaction with high signal-to-noise, evanescent illumination or confocal imaging may be employed. The formation of a closed-complex on localized template nucleic acids may be observed as an increased fluorescence compared to the background, for instance, whereas in some instances it may be also be observed as a decreased fluorescence due to quenching or change in local polar environment. Optionally, a fraction of polymerase molecules may be tagged with a fluorophore while another fraction may be tagged with a quencher in the same reaction mixture; wherein, the formation of closed-complex on a localized, clonal population of nucleic acid is revealed as decrease in fluorescence compared to the background. The clonal population of nucleic acids may be attached to a support surface such as a planar substrate, microparticle, or nanoparticle. Optionally, a polymerase is tagged with a fluorophore, luminophore, chemiluminophore, chromophore, or bioluminophore. A ternary complex that includes a primed template nucleic acid molecule, a cognate nucleotide, and a fluorescently tagged or labeled polymerase can be detected or monitored by detecting the fluorescent label moiety attached to the polymerase.

Optionally, a plurality of template nucleic acids is tethered to a surface and one (or more) dNTPs are flowed in sequentially. The spectrum of affinities reveals the identity of the next correct nucleotide and therefore the next base in the template nucleic acid. Optionally, the affinities are measured without needing to remove and replace reaction mixture conditions (i.e., a wash step). Autocorrelation of the measured intensities of the binding interaction, for instance, could readily reveal the dynamics of nucleic acid sequence. Optionally, examination includes monitoring the affinity of the polymerase to the primed template nucleic acid in the presence of nucleotides. Optionally, the polymerase binds transiently with the nucleic acid and the binding kinetics and affinity provides information about the identity of the next base on the template nucleic acid. Optionally, a closed-complex is formed, wherein the reaction conditions involved in the formation of the closed-complex provide information about the next base on the nucleic acid. Optionally, the polymerase is trapped at the polymerization site in its the interaction, thus revealing the affinities without requiring a washing step to measure the off-rate.

Any technique that can measure dynamic interactions between a crippled DNA polymerase and nucleic acid may be used to measure the affinities and enable the sequencing reaction methods disclosed herein.

Systems for Detecting Nucleotide-Specific Ternary Complex Formation

The provided methods can be performed using a platform, where any component of the nucleic acid polymerization reaction is localized to a surface. Optionally, the template nucleic acid is attached to a planar substrate, a nanohole array, a microparticle, or a nanoparticle. Optionally, all reaction components are freely suspended in the reaction mixture, and not immobilized to a solid support substrate.

Optionally, the template nucleic acid is immobilized to a surface. The surface may be a planar substrate, a hydrogel, a nanohole array, a microparticle, or a nanoparticle. Optionally, the reaction mixtures contain a plurality of clonally amplified template nucleic acid molecules. Optionally, the reaction mixtures contain a plurality of distinguishable template nucleic acids.

Provided herein, inter alia, are systems for performing sequencing reactions involving the examination of the interaction between a polymerase and a primed template nucleic acid in the presence of nucleotides to identify the next base in the template closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped polymerase complex provides information about the identity of the next base on the nucleic acid template.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanostructure. Optionally, the system includes one or more reagents and instructions necessary to bind template DNA molecules onto a nanostructure. For example, the system provides a nanostructure, such as a chip, configured for use with surface plasmon resonance to determine binding kinetics. An example of such a chip is a CM5 Sensor S chip (GE Healthcare; Piscatawany, N.J.). The system may provide instrumentation such as a surface plasmon resonance instrument. The system may provide streptavidin and/or biotin. Optionally, the system provides biotin-DNA, DNA ligase, buffers, and/or DNA polymerase for preparation of biotinylated template DNA. Optionally, the system provides a gel or reagents (e.g., phenol:chloroform) for biotinylated DNA purification. Alternatively, the system provides reagents for biotinylated template DNA characterization, for example, mass spectrometry or HPLC. Optionally, the system includes streptavidin, a chip, reagents, instrumentation, and/or instructions for immobilization of streptavidin on a chip. Optionally, a chip is provided in the system already configured for template DNA coating, wherein the chip is immobilized with a reagent capable of binding template nucleic acids or modified template nucleic acids (e.g., biotinylated template DNA). Optionally, the system provides reagents for chip regeneration.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanoparticle. Optionally, the system includes one or more reagents and instructions necessary to bind template DNA molecules onto a nanoparticle. The nanoparticle may be configured for the electrochemical detection of nucleic acid-polymerase interaction, for instance, by using gold nanoparticles. Optionally, the DNA-nanoparticle conjugates are formed between aqueous gold colloid solutions and template DNA molecules including, for example, free thiol or disulfide groups at their ends. The conjugates may include the same nucleic acid sequences. Optionally, the nanoparticle conjugates are stabilized against flocculation and precipitation at high temperature (e.g., greater than 60° C.) and high ionic strength (e.g., 1M $Na^+$). Optionally, the system provides reagents for preparing template DNA molecules for nanoparticle attachment, including, generating template DNA molecules with disulfides or thiols. Disulfide-containing template nucleic acids may be synthesized using, for example, a 3'-thiol modifier controlled-pore glass (CPG) or by beginning with a universal support CPG and adding a disulfide modifier phosphoramidite as the first monomer in the sequence. The system may provide nucleic acid synthesis reagents and/or instructions for obtaining disulfide-modified template nucleic acids. Thiol-containing template nucleic acids may also be generated during nucleic acid synthesis with a 5'-tritylthiol modifier phosphoramidite. The system may provide reagents and/or instructions for nanoparticle conjugate purification using for example, electrophoresis or centrifugation. Optionally, nanoparticle conjugates are used to monitor polymerase-template nucleic acid interactions colorimetrically. In this instance, the melting temperature of the nanoparticle conjugate increases in the presence of strong polymerase binding. Therefore, the strength of DNA binding can be determined by the change in this melting transition, which is observable by a color change. The systems optionally include reagents and equipment for detection of the melting transition.

Also provided is a system for performing one or more steps of any sequencing method disclosed herein. Optionally, the system includes components and reagents necessary to perform a polymerase and template nucleic acid binding assay in the presence of nucleotides, using a detectable polymerase. Optionally, the polymerase is detectably labeled. Optionally, the polymerase is detected using intrinsic properties of the polymerase, for example, aromatic amino acids. Optionally, the polymerase and template nucleic acids present in the system are configured for use in solution, without conjugation to a support. The detectable label on the polymerase may be a fluorophore, wherein fluorescence is used to monitor polymerase-template nucleic acid binding events. Optionally, the detectable polymerase may be used in combination with template nucleic acids in solution, or template nucleic acids conjugated to a support structure. Optionally, one or more cysteine residues of the polymerase is labeled with Cy3-maleimide. Optionally, the system includes reagents and/or instructions necessary to prepare fluorescently labeled polymerase molecules. The system may include reagents and/or instructions for purification of fluorescently labeled polymerases.

Procedural Features of the Methods

Following the examination step, where the identity of the next base has been identified via formation of a closed-complex, the reaction conditions may be reset, recharged, or modified as appropriate, in preparation for the optional incorporation step or an additional examination step. Optionally, the identity of the next base has been identified without chemically incorporating a nucleotide. Optionally, the identity of the next base is identified with chemical incorporation of a nucleotide, wherein a subsequent nucleotide incorporation has been inhibited. Optionally, all components of the examination step, excluding the template nucleic acid being sequenced, are removed or washed away, returning the system to the pre-examination condition. Optionally, partial components of the examination step are removed. Optionally, additional components are added to the examination step.

Optionally, reversible terminator nucleotides are used in the incorporation step to ensure one, and only one nucleotide is incorporated per cycle. No labels are required on the reversible terminator nucleotides as the base identity is known from the examination step. Non-fluorescently labeled reversible terminators are readily available from commercial suppliers. Non-labeled reversible terminator nucleotides are expected to have much faster incorporation kinetics compared to labeled reversible terminators due to their smaller steric footprint, and similar size to natural nucleotides.

Disclosed herein, in part, are reagent cycling sequencing methods, wherein sequencing reagents are introduced, one after another, for every cycle of examination and/or incorporation. Optionally, the sequencing reaction mixture includes a polymerase, a primed template nucleic acid, and at least one type of nucleotide. Optionally, the nucleotide and/or polymerase are introduced cyclically to the sequencing reaction mixture. Optionally, the sequencing reaction mixture includes a plurality of polymerases, primed template nucleic acids, and nucleotides. Optionally, a plurality of nucleotides and/or a plurality of polymerases are introduced cyclically to the sequencing reaction mixture. Optionally, the examination step of the sequencing reaction has a different composition than the incorporation step of the sequencing reaction.

Optionally, one or more nucleotides are sequentially added to and removed from the sequencing reaction. Optionally, 1, 2, 3, 4, or more types of nucleotides are added to and removed from the reaction mixture. For example, one type of nucleotide is added to the sequencing reaction, removed, and replaced by another type of nucleotide. Optionally, a nucleotide type present during the examination step is different from a nucleotide type present during the incorporation step. Optionally, a nucleotide type present during one examination step is different from a nucleotide type present during a sequential examination step (i.e., the sequential examination step is performed prior to an incorporation step). Optionally, 1, 2, 3, 4 or more types of nucleotides are present in the examination reaction mixture and 1, 2, 3, 4, or more types of nucleotides are present in the incorporation reaction mixture.

Optionally, a crippled DNA polymerase is cyclically added to and removed from the sequencing reaction. One or more different types of polymerases may be cyclically added to and removed from the sequencing reaction. Optionally, a polymerase type present during the examination step is different from a polymerase type present during the incorporation step. A polymerase type present during one examination step may be different from a polymerase type present during a sequential examination step (i.e., the sequential examination step is performed prior to an incorporation step).

Optionally, conditions such as the presence of reagents, pH, temperature, and ionic strength are varied throughout the sequencing reaction. Optionally, a metal is cyclically added to and removed from the sequencing reaction. For example, a catalytic metal ion may be absent during an examination step and present during an incorporation step. Alternatively, a polymerase inhibitor may be present during an examination step and absent during an incorporation step. Optionally, reaction components that are consumed during the sequencing reaction are supplemented with the addition of new components at any point during the sequencing reaction.

Nucleotides can be added one type at a time, with the crippled DNA polymerase, to a reaction condition that favors closed-complex formation. The polymerase binds only to the template nucleic acid if the next correct nucleotide is present. A wash step after every nucleotide addition ensures all excess polymerases and nucleotides not involved in a closed-complex are removed from the reaction mixture. If the nucleotides are added one at a time, in a known order, the next base on the template nucleic acid is determined by the formation of a closed-complex when the added nucleotide is the next correct nucleotide. The closed-complex may be identified by both the conformational change and the increased stability of the polymerase-template nucleic acid-nucleotide interaction. Optionally, the stability of the closed-complex formed in the presence of the next correct nucleotide is at least an order of magnitude greater than the unstable interactions of the polymerase with the template nucleic acid in the presence of incorrect nucleotides. The use of a wash step ensures that there are no unbound nucleotides and polymerases and that the only nucleotides present in the reaction are those sequestered in a closed-complex with a polymerase and a template nucleic acid. Once the next base on the template nucleic acid is determined, the next correct nucleotide sequestered in the closed-complex may be incorporated by flowing in reaction conditions that favor dissociation or destabilization of the closed-complex and extending the template nucleic acid primer strand by one base (incorporation). Therefore, the wash step ensures that the only nucleotide incorporated is the next correct nucleotide from the closed-complex. This reagent cycling method may be repeated and the nucleic acid sequence determined. This reagent cycling method may be applied to a single template nucleic acid molecule, or to collections of clonal populations such as PCR products or rolling-circle amplified DNA. Many different templates can be sequenced in parallel if they are arrayed, for instance, on a solid support. Optionally, the wash step destabilizes binary complex formation. Optionally, the washing is performed for a duration of time that ensures that the binary complex is removed, leaving the stabilized closed-complex in the reaction mixture. Optionally, the wash step includes washing the reaction with a high ionic strength or a high pH solution.

Optionally, the incorporation step is a three stage process. In the first stage, all four nucleotide types are introduced into a reaction including a primed template nucleic acid, with a crippled DNA polymerase, under reaction conditions which favor the formation of a closed-complex, and the next correct nucleotides are allowed to form stable closed-complexes with the template nucleic acid. In a second stage, the crippled DNA polymerase and any cognate nucleotide that may have been present is removed, and the removed components are then replaced with a second polymerase and one or more nucleotides (e.g., reversible terminator nucleotides). In a third stage, cognate nucleotide is incorporated into the 3'-end of the template nucleic acid primer. Formation of tight polymerase-nucleic acid complexes in the incorporation step can be enabled by standard techniques such as fusing a non-specific DNA binding domain to the polymerase (e.g., the Phusion polymerase, which is available from Thermo Fisher Scientific; Waltham, MA), and utilizing high concentrations of nucleotides to ensure correct nucleotides are always present in the closed-complex.

Polymerase molecules bind to primed template nucleic acid molecules in a fingers-closed conformation in the presence of the next correct nucleotide even in the absence of divalent metal ions that are typically required for polymerase synthesis reactions. The conformational change traps the nucleotide complementary to the next template base within the active site of the polymerase. Optionally, the formation of the closed-complex may be used to determine the identity of next base on the template nucleic acid. Optionally, the primed template nucleic acids may be contacted serially by different nucleotides in the presence of polymerase, in the absence of catalytic divalent metal ions; wherein the formation of a closed-complex indicates the nucleotide currently in contact with the template nucleic acid is the complementary nucleotide to the next base on the nucleic acid. A known order of nucleotides (in the presence of polymerase and absence of catalytic metal ions) brought into contact with the template nucleic acid ensures facile identification of the complementary nucleotide based on the particular position in the order that induces closed-complex formation. Optionally, an appropriate wash step may be performed after every nucleotide addition to ensure removal of all excess enzymes and nucleotides, leaving behind only the polymerase that is bound to nucleic acids in a closed-complex with the next correct nucleotide at the active site. The closed-complex may be identified by means that reveal the conformational change of the polymerase in the closed conformation or by means that reveal the increased stability of the polymerase/nucleic-acid/next-correct-nucleotide complex compared to binary polymerase-nucleic acid complexes or compared to unstable interactions between the polymerase, primed template nucleic acid and incorrect nucleotides.

Optionally, the process of identifying the next complementary nucleotide (examination step) includes the steps of contacting immobilized primed template nucleic acids with an examination mixture including polymerase and nucleotides of one kind under conditions that inhibit the chemical incorporation of the nucleotide, removing unbound reagents by a wash step, detecting the presence or absence of polymerase closed-complex on the immobilized nucleic acids, and repeating these steps serially, with nucleotides of different kinds until a closed-complex formation is detected. The closed-complex may be identified by both the conformational change and the increased stability of the polymerase/nucleic acid/next-correct-nucleotide complex. The wash step between successive nucleotide additions may be eliminated by the use of detection mechanisms that can detect the formation of the closed-complex with high fidelity, for instance, evanescent wave sensing methods or methods that selectively monitor signals from the closed-complex. The examination steps noted above may be followed by an incorporation step including, contacting the closed-complex with catalytic metal ions (e.g., $Mn^{2+}$) to covalently add the nucleotide sequestered in the closed-complex to the 3'-end of the primer. Optionally, the incorporation step may include, contacting the immobilized nucleic acids with a pre-incorporation mixture including a combination of multiple types of nucleotides and polymerase under conditions that inhibit the chemical incorporation of the nucleotides; wherein the pre-incorporation mixture may contain additives and solution conditions to ensure highly efficient closed-complex formation (e.g., low-salt conditions). The methods may also include performing a wash step to remove unbound reagents and providing the immobilized complexes with an incorporation mixture, including catalytic metal ions, to chemically incorporate nucleotides sequestered within the active site of the polymerase. The pre-incorporation mixture ensures highly efficient closed-complex formation, while the wash step and incorporation mixture ensure the addition of a single nucleotide to the 3'-end of the primer. Optionally, the incorporation step may occur directly after examination an addition of one type of nucleotide. For instance, a repeated pattern used for sequencing may include the following flow pattern (i) dATP+/polymerase, (ii) Wash, (iii) $Mn^{+2}$, (iv) Wash, (v) dTTP+/polymerase, (vi) Wash, (vii) $Mn^{+2}$, (viii) Wash, (ix) dCTP+/polymerase, (x) Wash (xi) $Mn^{-2}$, (xii) Wash, (xiii) dGTP+/polymerase, (xiv) Wash, (xv) $Mn^{+2}$, (xvi) Wash. Optionally, the repeated pattern used for sequencing may include (i) dATP+/polymerase, (ii) Wash, (iii) dTTP+/polymerase, (iv) Wash, (v) dGTP+/polymerase, (vi) Wash, (vii) dCTP+/polymerase, (viii) Wash, (ix) Pre-incorporation mixture, (x) Wash, (xi) $Mn^{2+}$, (xii) Wash. The wash steps optionally contain metal ion chelators and other small molecules to prevent accidental incorporations during the examination steps. After the incorporation step, the primer strand is typically extended by one base. Repeating this process, sequential nucleobases of a nucleic acid may be identified, effectively determining the nucleic acid sequence. Optionally, the examination step is performed at high salt conditions, for example, under conditions of 50 mM to 1,500 mM salt.

For sequencing applications, it can be advantageous to minimize or eliminate fluidics and reagents exchange. Removing pumps, valves and reagent containers can allow for simplified manufacturing of smaller devices. Disclosed herein, in part, are "all-in" sequencing methods, wherein the need to introduce reagents one after another, for every cycle of examination and/or incorporation, is eliminated. Reagents are added only once to the reaction, and sequencing-by-synthesis is performed by manipulating reagents already enclosed within the sequencing reaction. A scheme such as this requires a method to distinguish different nucleotides, a method to synchronize incorporation of nucleotides across a clonal population of nucleic acids and/or across different nucleic acid molecules, and a method to ensure only one nucleotide is added per cycle.

Optionally, the sequencing reaction mixture includes a crippled DNA polymerase, a primed template nucleic acid, and at least one type of nucleotide. Optionally, the sequencing reaction mixture includes a plurality of polymerases, primed template nucleic acids, and nucleotides. As provided herein, a polymerase refers to a single polymerase or a plurality of polymerases. As provided herein, a primed template nucleic acid or template nucleic acid refers to a single primed template nucleic acid or single template nucleic acid, or a plurality of primed template nucleic acids or a plurality of template nucleic acids. As provided herein, a nucleotide refers to one nucleotide or a plurality of nucleotides. As provided herein, a single nucleotide is one nucleotide. Optionally, the sequencing reaction nucleotides include, but are not limited to, 1, 2, 3, or 4 of the following nucleotides: dATP, dGTP, dCTP, dTTP, and dUTP.

Optionally, 1, 2, 3, 4 or more types of nucleotides (e.g., dATP, dGTP, dCTP, dTTP) are present in the reaction mixture together at the same time, wherein one type of nucleotide is a next correct nucleotide. The reaction mixture further includes at least one crippled DNA polymerase and at least one primed template nucleic acids. Optionally, the template nucleic acid is a clonal population of template nucleic acids. Optionally, the crippled DNA polymerase, primed template nucleic acid, and the nucleotide form a closed-complex under examination reaction conditions.

In the provided methods, four types of nucleotides can be present at distinct and different concentrations wherein the diffusion and binding times of the polymerase to the template nucleic acid are different for each of the four nucleotides, should they be the next correct nucleotide, due to the different concentrations of the four nucleotides. For example, the nucleotide at the highest concentration would bind to its complementary base on the template nucleic acid at a fast time, and the nucleotide at the lowest concentration would bind to its complementary base on the template nucleic acid at a slower time; wherein binding to the complementary base on the template nucleic acid refers to the polymerase binding to the template nucleic acid with the next correct nucleotide in a closed closed-complex. The identity of the next correct nucleotide is therefore determined by monitoring the rate or time of binding of polymerase to the template nucleic acid in a closed-complex. Optionally, the four types of nucleotides may be distinguished by their concentration, wherein the different concentrations of the nucleotides result in measurably different on-rates for the polymerase binding to the nucleic acid. Optionally, the four types of nucleotides may be distinguished by their concentration, wherein the different concentrations of the nucleotides result in measurably different on-rates for the formation of a stabilized closed-complex.

Optionally, the crippled DNA polymerase is labeled. In some instances, the polymerase is not labeled (i.e., does not harbor an exogenous label, such as a fluorescent label) and any label-free detection method disclosed herein or known in the art is employed. Optionally, the binding of the polymerase to the nucleic acid is monitored via a detectable feature of the crippled DNA polymerase. Optionally, the formation of a stabilized closed-complex is monitored via a detectable feature of the polymerase. A detectable feature of the polymerase may include, but is not limited to, optical, electrical, thermal, colorimetric, mass, and any combination thereof.

Optionally, 1, 2, 3, 4, or more nucleotides types (e.g., dATP, dTTP, dCTP, dGTP) are tethered to 1, 2, 3, 4, or more different crippled DNA polymerase; wherein each nucleotide type is tethered to a different polymerase and each polymerase has a different exogenous label or a detectable feature from the other polymerases to enable its identification. All tethered nucleotide types can be added together to a sequencing reaction mixture forming a closed-complex including a tethered nucleotide-polymerase; the closed-complex is monitored to identify the polymerase, thereby identifying the next correct nucleotide to which the polymerase is tethered. The tethering may occur at the gamma phosphate of the nucleotide through a multi-phosphate group and a linker molecule. Such gamma-phosphate linking methods are standard in the art, where a fluorophore is attached to the gamma phosphate linker. Optionally, different nucleotide types are identified by distinguishable exogenous labels. Optionally, the distinguishable exogenous labels are attached to the gamma phosphate position of each nucleotide.

Optionally, the sequencing reaction mixture includes a catalytic metal ion. Optionally, the catalytic metal ion is $Mn^{2+}$ ion. Optionally, the catalytic metal ion is available to react with a crippled DNA polymerase at any point in the sequencing reaction in a transient manner. To ensure robust sequencing, the catalytic metal ion is available for a brief period of time, allowing for a single nucleotide complementary to the next base in the template nucleic acid to be incorporated into the 3'-end of the primer during an incorporation step. In this instance, no other nucleotides, for example, the nucleotides complementary to the bases downstream of the next base in the template nucleic acid, are incorporated. Optionally, the catalytic metal ion magnesium is present as a photocaged complex (e.g., DM-Nitrophen) in the sequencing reaction mixture such that localized UV illumination releases the magnesium, making it available to the polymerase for nucleotide incorporation. Furthermore, the sequencing reaction mixture may contain EDTA, wherein the magnesium is released from the polymerase active site after catalytic nucleotide incorporation and captured by the EDTA in the sequencing reaction mixture, thereby rendering magnesium incapable of catalyzing a subsequent nucleotide incorporation.

Thus, in the provided methods, a catalytic metal ion can be present in a sequencing reaction in a chelated or caged form from which it can be released by a trigger. For example, the catalytic metal ion catalyzes the incorporation of the closed-complex next correct nucleotide, and, as the catalytic metal ion is released from the active site, it is sequestered by a second chelating or caging agent, disabling the metal ion from catalyzing a subsequent incorporation. The localized release of the catalytic metal ion from its cheating or caged complex is ensured by using a localized uncaging or un-chelating scheme, such as an evanescent wave illumination or a structured illumination. Controlled release of the catalytic metal ions may occur for example, by thermal means. Controlled release of the catalytic metal ions from their photocaged complex may be released locally near the template nucleic acid by confined optical fields, for instance by evanescent illumination such as waveguides or total internal reflection microscopy. Controlled release of the catalytic metal ions may occur for example, by altering the pH of the solution near the vicinity of the template nucleic acid. Chelating agents such as EDTA and EGTA are pH dependent. At a pH below 5, divalent cations $Mg^{2-}$ and $Mn^{2+}$ are not effectively chelated by EDTA. A method to controllably manipulate the pH near the template nucleic acid allows the controlled release of a catalytic metal ion from a chelating agent. Optionally, the local pH change is induced by applying a voltage to the surface to which the nucleic acid is attached. The pH method offers an advantage in that that metal goes back to its chelated form when the pH is reverted back to the chelating range.

Described above are polymerase-nucleic acid binding reactions for the identification of a nucleic acid sequence.

However, nucleic acid sequence identification may include information regarding nucleic acid modifications, including methylation and hydroxymethylation. Methylation may occur on cytosine bases of a template nucleic acid. DNA methylation may stably alter the expression of genes. DNA methylation is also indicated in the development of various types of cancers, atherosclerosis, and aging. DNA methylation therefore can serve as an epigenetic biomarker for human disease.

Optionally, one or more cytosine methylations on a template nucleic acid are identified during the sequencing by binding methods provided herein. The template nucleic acid may be clonally amplified prior to sequencing, wherein the amplicons include the same methylation as their template nucleic acid. Amplification of the template nucleic acids may include the use of DNA methyltransferases to achieve amplicon methylation. The template nucleic acids or amplified template nucleic acids are provided to a reaction mixture including a polymerase and one or more nucleotide types, wherein the interaction between the polymerase and nucleic acids is monitored. Optionally, the interaction between the polymerase and template nucleic acid in the presence of a methylated cytosine is different than the interaction in the presence of an unmodified cytosine. Therefore, based on examination of a polymerase-nucleic acid interaction, the identity of a modified nucleotide is determined.

Optionally, following one or more examination and/or incorporation steps, a subset of nucleotides is added to reduce or reset phasing. Thus, the methods can include one or more steps of contacting a template nucleic acid molecule being sequenced with a composition comprising a subset of nucleotides and an enzyme for incorporating the nucleotides into the strand opposite the template strand of the nucleic acid molecule. The contacting can occur under conditions to reduce phasing in the nucleic acid molecule. Optionally, the step of contacting the template nucleic acid molecule occurs after an incorporation step and/or after an examination step. Optionally, the contacting occurs after 1, 2, 3, 4, 5, 6, 7, 8, 9, 10, 15, 20, 25, 30, 35, 40, 45, 50, 60, 65, 70, 75, 80, 85, 90, 95, or 100 rounds or more of sequencing (i.e., rounds of examination and incorporation). Optionally, the contacting occurs after 30 to 60 rounds of sequencing. Optionally, the contacting occurs after every round of sequencing (i.e., after one set of examination and incorporation steps). Optionally, multiple contacting steps occur after every round of sequencing, wherein each contacting step may comprise different subsets of nucleotides. Optionally, the method further comprises one or more washing steps after contacting. Optionally, the subset comprises two or three nucleotides. Optionally, the subset comprises three nucleotides. Optionally, the subset of nucleotides is selected from three of dATP, dGTP, dCTP, dTTP or a derivative thereof. Optionally, the three nucleotides comprise adenosine, cytosine, and guanine. Optionally, the three nucleotides comprise adenosine, cytosine, and thymine. Optionally, the three nucleotides comprise cytosine, guanine and thymine. Optionally, the three nucleotides comprise adenosine, guanine and thymine. Optionally, each round of contacting comprises the same subset or different subsets of nucleotides. Optionally, sequencing of a nucleic acid template is monitored and the contacting with the subset of nucleotides occurs upon detection of phasing. See also for example, U.S. Pat. No. 8,236,532, which is incorporated herein by reference in its entirety.

Optionally, the sequencing reaction involves a plurality of template nucleic acids, polymerases and/or nucleotides, wherein a plurality of closed-complexes is monitored. Clonally amplified template nucleic acids may be sequenced together wherein the clones are localized in close proximity to allow for enhanced monitoring during sequencing. Optionally, the formation of a closed-complex ensures the synchronicity of base extension across a plurality of clonally amplified template nucleic acids. The synchronicity of base extension allows for the addition of only one base per sequencing cycle.

Genotyping Applications

Exemplary uses for the disclosed crippled DNA polymerases relate to SNP detection and genotyping applications, without necessitating extensive sequence determination. Here the crippled DNA polymerase can be used for determining, without incorporation, the identity of the next correct nucleotide for a primed template nucleic acid molecule undergoing examination. Optionally, the procedure involves hybridizing a primer to a target nucleic acid to result in the primed template nucleic acid molecule. The primed template nucleic acid can then be contacted with a composition that includes the crippled DNA polymerase and one of more nucleotides. Optionally, the crippled DNA polymerase includes a detectable label, such as a fluorescent detectable label. Optionally, more than one crippled DNA polymerase is included in the composition, where at least two of the crippled DNA polymerases are distinguishably labeled. Optionally, the composition includes at least one nucleotide that harbors a detectable label, such as a detectable fluorescent label. Optionally, more than one nucleotide in the composition includes a detectable label. Optionally, two different nucleotides in the composition each harbor different detectable labels that can be distinguished from each other. Commonly owned U.S. patent application identified by Ser. No. 62/448,630 (filed Jan. 20, 2017), the disclosure of which is incorporated by reference, sets forth numerous genotyping procedures wherein the instant crippled DNA polymerases can be used.

Illustrative Sequencing Methods Employing a Crippled DNA Polymerase

Examination reactions in accordance with the disclosed technique optionally can be conducted in the presence of $Mg^{2+}$ ion. The fact that the crippled DNA polymerase cannot catalyze phosphodiester bond formation in the presence of this ion means that it can be included during the examination step without compromising transient binding (i.e., binding without incorporation). The presence of the catalytic metal ions may enhance the discriminatory activities that are ordinarily important during the DNA polymerization reaction. While non-catalytic ions also may be included or substituted in place of the catalytic ions, inclusion of the non-catalytic metal ions that inhibit polymerase-mediated incorporation is optional.

Examination reactions using the disclosed technique optionally can be conducted using native nucleotides. Generally speaking, any method for detecting a ternary complex that includes the crippled DNA polymerase will be useful in the nucleotide sequence determination protocol. Optical techniques detecting changes in refractive index (e.g., interferometry or surface plasmon resonance sensing) will be capable of label-free detection, and so can be carried out using unlabeled native nucleotides in the examination step. Optionally, if the crippled DNA polymerase harbors an exogenous label (e.g., a fluorescent label), then formation of a ternary complex localized to a defined position on a solid support or surface (e.g., a locus on a planar array, or a bead array) can be detected using conventional fluorescent monitoring techniques.

Examination reactions conducted using crippled polymerases optionally can be carried out using nucleotides that harbor an exogenous label (e.g., a fluorescent label). When used with a fluorescent detection platform, nucleotide analogs harboring fluorescent chemical moieties that co-localize with the primed template nucleic acid and the crippled polymerase can indicate ternary complex formation.

Examination can be conducted using primed template nucleic acids, where the primer strand of the duplex harbors a free 3' hydroxyl moiety that is available to participate in formation of a phosphodiester bond in the presence of a cognate nucleotide and a native DNA polymerase having the capability of forming phosphodiester bonds.

An exemplary work flow for the sequencing technique would involve first contacting a primed template nucleic acid with one or more test nucleotides (i.e., nucleotides being tested as cognate nucleotide candidates), and the crippled polymerase. In the event the test nucleotide is the next correct nucleotide, a ternary complex that includes all three components will be formed. Affirmative detection of the ternary complex indicates that the test nucleotide is the cognate nucleotide harboring a base complementary to that position along the template strand. Since the crippled DNA polymerase will be incapable of catalyzing a phosphodiester bond, identification of the next correct nucleotide necessarily will take place without incorporation of the cognate nucleotide into the primer. Extending the primer by incorporation of the cognate nucleotide can be accomplished by different approaches. For example, once information needed to identify the next correct nucleotide has been gathered, an exchange of reaction mixtures can be effected so that the crippled polymerase is exchanged for a second polymerase able to promote phosphodiester bond formation. If also provided with cognate nucleotide and a divalent cation, the second polymerase will be able to effect incorporation of the cognate nucleotide into the primer.

It is to be understood that the disclosed technique will require an active DNA polymerizing enzyme for incorporating cognate nucleotide into the growing primer.

In certain embodiments of the disclosed technique, a reversible terminator nucleotide corresponding to the cognate nucleotide can be incorporated into the growing primer once information needed to establish identity of the cognate nucleotide has been gathered.

In one aspect, the disclosed technique features nucleotide identification by a procedure that relies on use of a crippled DNA polymerase. Optionally, $Mg^{2+}$ ions can be included in the examination reaction mixture that further includes the primed template nucleic acid, crippled DNA polymerase, and test nucleotide. Optionally, the primed template nucleic acid can be immobilized at a fixed position on a planar surface or a bead. Optionally, the test nucleotides used in the examination step are native nucleotides. Optionally, the test nucleotides include an exogenous label, such as a fluorescent label. Optionally, different test nucleotides are labeled with different exogenous labels that are distinguishable from each other. Optionally, the primer of the primed template nucleic acid includes a free 3' hydroxyl group. Optionally, the crippled DNA polymerase harbors an exogenous label, such as a fluorescent label. Optionally, once sufficient information has been gathered to identify a cognate nucleotide present in a ternary complex that includes the primed template nucleic acid, the crippled DNA polymerase, and the nucleotide, the crippled DNA polymerase and the nucleotide can be removed from the primed template nucleic acid (e.g., by the use of EDTA and high ionic strength conditions) and replaced with a second polymerase and one or another type of nucleotide. The second DNA polymerase optionally will be capable of catalyzing phosphodiester bond formation. Nucleotides used in conjunction with the second DNA polymerase can be either native nucleotides or nucleotide analogs (e.g., reversible terminator nucleotides). Optionally, using the crippled DNA polymerase and the second DNA polymerase in a cycling protocol permits extension of the primer by incorporation of one or more nucleotides. Optionally, use of the second DNA polymerase in combination with reversible terminator nucleotides restricts the incorporation to a single nucleotide. Optionally, the reversible terminator moiety can be removed to permit subsequent incorporation of another nucleotide or nucleotide analog.

Example 1 illustrates how a crippled polymerase can be used in a DNA sequencing method with fluorescently labeled nucleotides.

Example 1

DNA Sequence Determination Using a Crippled DNA Polymerase and Fluorescent Nucleotides A crippled DNA polymerase possessing cognate nucleotide binding and discrimination activities, but not the ability to form phosphodiester bonds first is obtained. A primed template nucleic acid immobilized at a defined position on a solid support in an array format of a flow cell is contacted with a first reaction mixture that includes the crippled polymerase, and dATP labeled with a fluorescent moiety on the gamma phosphate. Fluorescence monitoring indicates no fluorescence signal above background. This indicates that dATP is not the next correct nucleotide. The first reaction mixture within the flow cell is replaced by a second reaction mixture that includes the crippled polymerase, and dGTP labeled with a fluorescent moiety on the gamma phosphate. Fluorescence monitoring indicates substantial fluorescence above background. This indicates that dGTP is the next correct nucleotide. The second reaction mixture is flushed from the flow cell and replaced by an incorporation reaction mixture that includes Therminator DNA polymerase (New England BioLabs) and four reversible terminator nucleotides, each having a 3'-$ONH_2$ blocking group. The reversible terminator nucleotide having guanine as its base is incorporated. Optionally, the resulting blocked primed template nucleic acid molecule is used directly in a subsequent round of nucleotide examination with the crippled DNA polymerase to obtain more extensive sequence information. Optionally, the reversible terminator moiety is chemically cleaved by standard procedures to reveal a native primer, and the resulting primed template nucleic acid molecule is used in a subsequent round of nucleotide examination with the crippled DNA polymerase to obtain more extensive sequence information.

Example 2 illustrates how a crippled polymerase can be used in a DNA sequencing method when the crippled polymerase is fluorescently labeled.

Example 2

DNA Sequence Determination Using a Fluorescently Labeled Crippled DNA Polymerase A crippled DNA polymerase possessing cognate nucleotide binding and discrimination activities, but not the ability to form phosphodiester bonds first is obtained. The crippled DNA polymerase is labeled with a fluorescent moiety on the functional group of a surface-accessible cysteine amino acid. A primed template nucleic acid immobilized at a defined position on a solid support in an array format of a flow cell is contacted with a first reaction mixture that includes the fluorescent crippled DNA polymerase, and native dATP. Fluorescence monitoring indicates no fluorescence signal above background. This indicates that dATP is not the next correct nucleotide. The first reaction mixture within the flow cell is replaced by a second reaction mixture that includes the fluorescent crippled polymerase, and native dGTP. Fluorescence monitoring indicates substantial fluorescence above background. This indicates that dGTP is the next correct nucleotide. The second reaction mixture is flushed from the flow cell and replaced by an incorporation reaction mixture that includes Therminator DNA polymerase (New England BioLabs) and four reversible terminator nucleotides, each having a 3'-ONH$_2$ blocking group. The reversible terminator nucleotide having guanine as its base is incorporated.

The above-described TDE mutant polymerase was prepared and purified using standard techniques that will be familiar to those having an ordinary level of skill in the art. The Bst-f protein backbone used in the procedure (i.e., SEQ ID NO:1) had been modified to include an optimized cysteine (cys) residue at position 23, a histidine-tag sequence at the N-terminus (i.e., positions 5-10) to aid in protein purification, and a thrombin cleave site between positions 16-17. None of the protein sequence modifications upstream of the first methionine of the native Bst DNA polymerase (i.e., position 27 of SEQ ID NO:1) was deemed essential for the desired combination of correct nucleotide identification without Mg$^{2+}$-catalyzed incorporation. Thus, inclusion of these modifications is optional in the working product, and so the three TDE mutants set forth in Table 1 (i.e., using the parent scaffolds of any of SEQ ID Nos:1-3) optionally may be used for carrying out detection or sequencing procedures.

Example 3 describes the use of crippled DNA polymerases in sequencing-by-binding protocols involving cycles of examination to identify cognate nucleotides, and demonstrates that the mutants do not incorporate cognate nucleotide in the presence of the otherwise catalytic Mg$^{2+}$ metal ion. As described above, the TDE mutant includes a single amino acid change at position 381 of the Bst-f enzyme (SEQ ID NO:1). Accordingly, the TDE mutant included the sequence EYSQIELR (SEQ ID NO:12) in place of DYSQIELR (SEQ ID NO:13) within motif A. The BDE mutant included the sequence QVHEEL (SEQ ID NO:14) in place of QVHDEL (SEQ ID NO:15) within motif C. The parent enzyme that included an exogenous cysteine residue and N-terminal His-tag, but did not include any polymerization-crippling mutation served as a control in this procedure. In alternatives, engineered polymerases including the modified motif A can be substituted in the procedure. For example, the engineered polymerase can include the sequence of SEQ ID NO:12 contained within the sequence of SEQ ID NO:3 having position 355 substituted by glutamate. The sequence of SEQ ID NO:2 having position 364 substituted by glutamate is one example, while the sequence of SEQ ID NO:1 having position 381 substituted by glutamate is another example. Likewise, engineered polymerases including the modified motif C can be substituted in the procedure. For example, the engineered polymerase can include the sequence of SEQ ID NO:14 contained within the sequence of SEQ ID NO:3 having position 532 substituted by glutamate. The sequence of SEQ ID NO:2 having position 541 substituted by glutamate is one example, while the sequence of SEQ ID NO:1 having position 558 substituted by glutamate is another example.

Example 3

Demonstration of Cognate Nucleotide Identification Without Incorporation Using a Crippled DNA Polymerase A FORTEBIO® (Menlo Park, CA) Octet instrument employing biolayer interferometry to measure binding reactions at the surface of a fiber optic tip was used in a multiwell plate format to illustrate the sequencing technique. Primed template nucleic acid molecules biotinylated at the 5'-ends of the template strand were immobilized onto fiber optic tips functionalized with streptavidin (SA) using standard procedures. The primed template nucleic acid molecule in this procedure had CG as the next correct nucleotides downstream of the primer.

The cycling procedure involved steps for: (1) washing/regenerating sensor tips; (2) forming ternary complexes that included polymerase and cognate nucleotides; and (3) washing with an EDTA solution to strip complexes from the primed template nucleic acid molecule. An incorporation step followed a complete round of binding and examination using the four dNTPs, one at a time. Sensor tips were washed/regenerated in a Tris-buffered solution (pH 8.0) that included KCl, potassium glutamate, and 0.01% Tween-20 before commencing the cycling protocol. The first incoming nucleotide was interrogated with 500 nM of either TDE or 500 nM of CBT in the presence of examination buffer (30 mM Tris-HCl (pH 8.0), 420 mM KCl, 160 mM potassium glutamate, 2 mM SrCl$_2$, 0.01% Tween-20, 0.1 mg/mL acetylated BSA, and 1 mM β-mercaptoethanol. Native nucleotides were employed in the procedure, and were contacted to the sensor tip in the following order: dATP, dCTP, dTTP, and dGTP. Each of the dNTPs was present at a concentration of 100 µM, except for dTTP, which was used at a concentration of 200 µM. Nucleotide binding steps were for a period of about 30 seconds at 30° C. At the end of each nucleotide binding and examination step, any formed complexes were washed from the sensor tip for 45 seconds using an EDTA solution containing KCl to chelate divalent cations. Thereafter, the biosensor was regenerated for 30 seconds before moving to the next dNTP exam.

Following examination of all four dNTPs to determine whether a ternary complex had formed, incorporation reactions were performed to investigate possible residual polymerase activity of the TDE mutant. Here the parent CBT enzyme served as a positive control for nucleotide binding and incorporation activities. First, ternary complexes were prepared by contacting the sensor tips with the cognate nucleotide (i.e., dCTP) at a concentration of 100 µM for 30 seconds. Next, biosensor tips were transferred to an incorporation buffer (30 mM Tris-HCl (pH 8.0), 50 mM KCl, 50 mM Mg$^{2+}$) for 30 seconds. Finally, complexes were washed from the sensor tips for 45 seconds using the EDTA solution containing KCl to chelate divalent cations. Again, the biosensor was regenerated for 30 seconds before moving to the next series of examination reactions using all four dNTPs, one at a time. Results from this latter set of examination reactions was informative regarding binding and incorporation activities of the mutant enzyme.

Results from the procedure, shown in FIG. 1, confirmed that the crippled polymerase correctly identified the cognate nucleotide, but was incapable of incorporating that nucleotide even in the presence of the catalytic Mg$^{2+}$ metal ion. The FIGURE shows examination traces for all four nucleotides conducted using the TDE and CBT polymerases. Formation of binary complexes before addition of nucleotide established baseline values for the comparison. Ternary complexes generated in the presence of dNTP indicated that both polymerases correctly identified dCTP as the cognate nucleotide. In all cases, non-cognate nucleotides were associated with substantially baseline binding signals. Following the step to permit incorporation, only the parent CBT enzyme was shown to possess catalytic activity. More specifically, the mutant TDE enzyme again identified dCTP as the cognate nucleotide for the primed template nucleic acid molecule. This indicated that no nucleotide had been incorporated by the mutant enzyme under incorporating conditions. Conversely, the parent CBT enzyme identified dGTP as the next correct nucleotide following incorporation. Thus, the crippled polymerase correctly performed the examination step without the ability to incorporate cognate nucleotide. Of course, a repetitive cycling procedure to conduct extensive sequence determination can use a different enzyme for the incorporation step. A reversible terminator nucleotide (e.g., an unlabeled reversible terminator nucleotide) may be used in the incorporation procedure.

Additional testing conducted at lower concentrations of catalytic metal ions was performed to investigate the ability of the crippled TDE polymerase to incorporate cognate nucleotides by phosphodiester bond formation. Here 10 mM concentrations of $MgCl_2$ or $MnCl_2$ were tested in the incorporation step. Again, the crippled TDE mutant failed to incorporate cognate nucleotide in the presence of the catalytic $Mg^{2+}$ metal ion. However, the TDE mutant incorporated cognate nucleotide in the presence of the catalytic $Mn^+$ metal ion. Significantly, parallel testing showed that the BDE mutant correctly identified cognate nucleotide during examination steps, but like the TDE mutant also was catalytically inactive in the presence of $Mg^{2+}$ ion. The TDN mutant was incapable of both identifying cognate nucleotide and catalyzing phosphodiester bond formation.

Disclosed above are materials, compositions, and components that can be used for, can be used in conjunction with, can be used in preparation for, or are products of the disclosed methods and compositions. It is to be understood that when combinations, subsets, interactions, groups, etc. of these materials are disclosed, and that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure, including steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein, and the material for which they are cited, are hereby specifically incorporated by reference in their entireties. All publications, patents, and patent applications mentioned in this specification are herein incorporated by reference to the same extent as if each individual publication, patent, or patent application was specifically and individually indicated to be incorporated by reference.

It is to be understood that the headings used herein are for organizational purposes only and are not meant to limit the description or claims.

A number of embodiments have been described. Nevertheless, it will be understood that various modifications may be made. Accordingly, other embodiments are within the scope of the claims.

---

What is claimed is:

1. A mutant DNA polymerase comprising a polypeptide sequence, said polypeptide sequence comprising SEQ ID NO:12,
wherein said mutant DNA polymerase forms ternary complexes with primed template nucleic acid molecules and cognate nucleotides, and
wherein said mutant DNA polymerase is incapable of magnesium-catalyzed phosphodiester bond formation.

2. The mutant DNA polymerase of claim 1, wherein the mutant DNA polymerase catalyzes formation of phosphodiester bonds in the presence of manganese ions.

3. The mutant DNA polymerase of claim 1, wherein the polypeptide sequence of the mutant DNA polymerase comprises SEQ ID NO:1 with the exception of comprising SEQ ID NO:12 and having glutamate at amino acid position 381.

4. The mutant DNA polymerase of claim 1, wherein the polypeptide sequence of the mutant DNA polymerase comprises SEQ ID NO:2 with the exception of comprising SEQ ID NO:12 and having glutamate at amino acid position 364.

5. The mutant DNA polymerase of claim 1, wherein the polypeptide sequence of the mutant DNA polymerase comprises SEQ ID NO:3 with the exception of comprising SEQ ID NO:12 and having glutamate at amino acid position 355.

6. The mutant DNA polymerase of claim 1, further comprising an exogenous label.

7. A ternary complex, comprising the mutant DNA polymerase of claim 1, a primed template nucleic acid and a next correct nucleotide for the primed template nucleic acid.

8. The ternary complex of claim 7, wherein the next correct nucleotide comprises an exogenous label.

9. The ternary complex of claim 7, wherein the mutant DNA polymerase comprises an exogenous label.

* * * * *